United States Patent
Ling et al.

(10) Patent No.: US 12,162,243 B2
(45) Date of Patent: Dec. 10, 2024

(54) SUPERHYDROPHOBIC PLATFORM FOR SENSING URINE METABOLITES AND TOXINS

(71) Applicant: Nanyang Technological University, Singapore (SG)

(72) Inventors: Xing Yi Ling, Singapore (SG); Yih Hong Lee, Singapore (SG); Nguan Soon Tan, Singapore (SG); Xuemei Han, Singapore (SG); Hiang Kwee Lee, Singapore (SG); Ya-Chuan Kao, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 404 days.

(21) Appl. No.: 16/958,287

(22) PCT Filed: Jan. 15, 2019

(86) PCT No.: PCT/SG2019/050022
§ 371 (c)(1),
(2) Date: Jun. 26, 2020

(87) PCT Pub. No.: WO2019/139543
PCT Pub. Date: Jul. 18, 2019

(65) Prior Publication Data
US 2021/0053317 A1    Feb. 25, 2021

(30) Foreign Application Priority Data
Jan. 15, 2018  (SG) .......................... 10201800322W

(51) Int. Cl.
*G01N 21/65*  (2006.01)
*B32B 5/16*  (2006.01)
(Continued)

(52) U.S. Cl.
CPC .............. *B32B 15/018* (2013.01); *B32B 5/16* (2013.01); *B82Y 15/00* (2013.01); *G01N 21/658* (2013.01);
(Continued)

(58) Field of Classification Search
CPC .... G01N 21/65; G01N 21/658; G01N 33/743; G01N 33/54373; G01N 2800/368;
(Continued)

(56) References Cited

U.S. PATENT DOCUMENTS

2007/0155021 A1 * 7/2007 Zhang .............. G01N 33/54373
977/902
2008/0266555 A1    10/2008 Murphy et al.
(Continued)

FOREIGN PATENT DOCUMENTS

CN      103945966      7/2014
CN      102990079 B    10/2014
(Continued)

OTHER PUBLICATIONS

Tan, J. M. R. et al., Phys. Chem. Chem. Phys. 2014, 26983-26990, 16.
(Continued)

*Primary Examiner* — Rebecca M Fritchman
(74) *Attorney, Agent, or Firm* — Thomas | Horstemeyer, LLP

(57) ABSTRACT

Disclosed herein is a composite superhydrophobic material comprising: a substrate layer comprising a set of positively or negatively charged functional groups; a metal nanoparticle coating on top of the substrate layer, comprising a set of negatively or positively charged functional groups; a metal layer on top of the metal nanoparticle coating; and a first superhydrophobic layer on top of the metal layer. Also disclosed herein is a method of making said material, and a
(Continued)

method of predicting increased risk of spontaneous miscarriage using said material.

22 Claims, 17 Drawing Sheets

(51) Int. Cl.
     *B32B 15/01*          (2006.01)
     *B82Y 15/00*          (2011.01)
     *G01N 33/74*          (2006.01)
     *B01D 15/32*          (2006.01)
     *B82Y 30/00*          (2011.01)

(52) U.S. Cl.
     CPC ......... *G01N 33/743* (2013.01); *B01D 15/325* (2013.01); *B32B 2307/73* (2013.01); *B82Y 30/00* (2013.01); *G01N 2021/655* (2013.01); *G01N 2800/368* (2013.01)

(58) Field of Classification Search
     CPC ............... G01N 2021/655; B32B 15/018; B32B 33/00; B32B 5/16; B32B 2307/73; B82Y 30/00; B82Y 15/00; B01D 15/325
     See application file for complete search history.

(56) References Cited

U.S. PATENT DOCUMENTS

| | | | |
|---|---|---|---|
| 2009/0291889 A1 | 11/2009 | Breit et al. | |
| 2012/0058697 A1 | 3/2012 | Strickland et al. | |
| 2012/0287427 A1* | 11/2012 | Li | B82Y 20/00 977/773 |
| 2018/0297321 A1* | 10/2018 | Jin | B05D 5/083 |

FOREIGN PATENT DOCUMENTS

| | | |
|---|---|---|
| CN | 104749154 A | 7/2015 |
| WO | 2013043133 | 3/2013 |
| WO | 2018199849 | 11/2018 |

OTHER PUBLICATIONS

Li, X. et al., Anal. Chem. 2014, 10437-10444, 86.
Tao, A. et al., Angew. Chem. Int. Ed. 2006, 4597-4601, 45.
Panácek, A. et al., Chem. Mater. 2014, 1332-1339, 26.
Ku, C. W. et al., BBA Clin. 2017, 48-55, 8.
Li, X. et al., Langmuir 2003, 4285-4290, 19.
Ee et al. "Superhydrophobic Surface-Enhanced Raman Scattering Platform Fabricated by Assembly of Ag Nanocubes for Trace Molecular Sensing", ACS Applied Materials and Interfacing, Oct. 17, 2013, 5:21, p. 11409-11418.
Leblanc "Immobilization of gold nanoparticles for colourimetric detection of biofilms on surfaces", Dec. 31, 2015.
International Search Report, PCT/SG2019/050022, dated Mar. 29, 2019.
Written Opinion, PCT/SG2019/050022, dated Mar. 29, 2019.
Chinese Office Action for related application No. 201980008466.7_dated Jan. 13, 2022.
Chinese Office Action for related application No. 201980008466.7_dated Jan. 13, 2022 (English translation).
Ryu, Jeongeun et al. "Nearly Perfect Durable Superhydrophobic Surfaces Fabricated by a Simple One-Step Plasma Treatment." Scientific reports vol. 7,1 1981. May 16, 2017, doi:10.1038/s41598-017-02108-1.
Ryu, J., Kim, K., Park, J. et al. Nearly Perfect Durable Superhydrophobic Surfaces Fabricated by a Simple One-Step Plasma Treatment. Sci Rep 7, 1981.
Japanese Office Action for related application No. 2020-539001_ dated Jan. 6, 2023.
X. Li et al., Anal. Chem. 2014, 86, 20, 10437-10444.

* cited by examiner

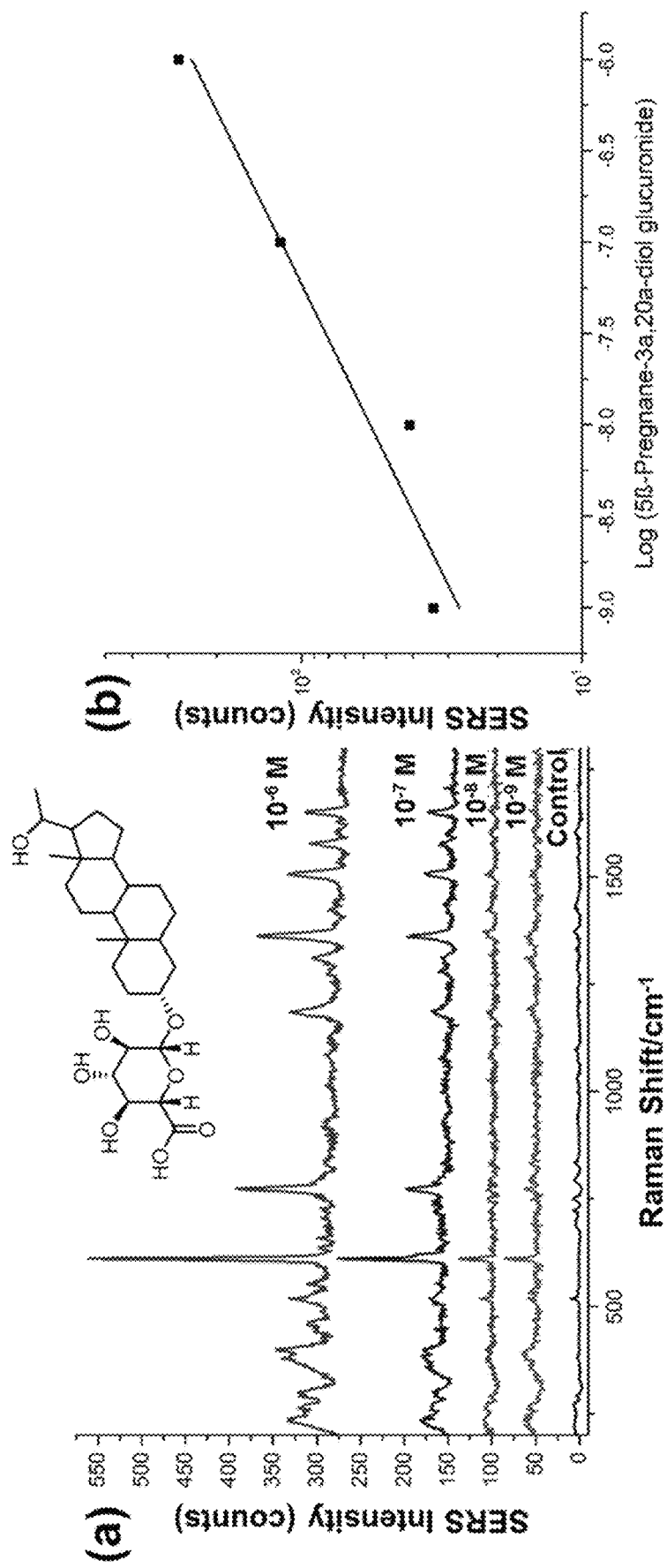
FIG. 13a-b

SUPERHYDROPHOBIC PLATFORM FOR SENSING URINE METABOLITES AND TOXINS

FIELD OF INVENTION

This invention relates to a composite superhydrophobic material suitable for use in surface-enhanced Raman scattering (SERS), a method of making said material, and its use for predicting increased risk of spontaneous miscarriage by SERS.

BACKGROUND

The listing or discussion of a prior-published document in this specification should not necessarily be taken as an acknowledgement that the document is part of the state of the art or is common general knowledge.

Spontaneous miscarriage accounts for approximately 25% of all threatened miscarriages. Threatened miscarriage is defined as an ongoing pregnancy with vaginal bleeding and may be accompanied by abdominal pain. Despite the high occurrence of spontaneous miscarriages, current prenatal care is unable to accurately identify pregnant women who are highly susceptible to spontaneous miscarriages.

In addition, the current management of spontaneous miscarriage may have also been over-medicalised. For instance, to reduce risks of miscarriage, patients are routinely prescribed progesterone analogues such as dydrogesterone, though there is no conclusive evidence that dydrogesterone can prevent or reduce the risk of miscarriage in patients presenting symptoms of threatened miscarriage. Further, most of these patients (about 75%) eventually proceed to have healthy births—with or without the prescription of dydrogesterone. As such, it appears that the current protocol places unnecessary stress and medical costs on patients who may not undergo spontaneous miscarriage, despite presenting symptoms of threatened miscarriage.

Recently, six urine metabolites were identified via liquid chromatography/mass spectrometry (LC/MS) to be associated with spontaneous miscarriage (see PCT publication number WO 2018/199849). Typically, pregnant women suffering from spontaneous miscarriages have higher levels of tetrahydrocortisone and hexanoylcarnitine, and lower level of 5β-pregnane-3α,20α-diol glucuronide, propionylcarnitine, isovalerycarnitine and 3-methylglutarylcarnitine, as compared to women with successful delivery.

However, the use of LC/MS to identify the target urine metabolites may be impractical and cannot be broadly applied in clinical settings. Firstly, the instrumentation is expensive (>S$500,000) and requires a large area (>1 $m^2$) to house the instruments. In addition, running the entire sampling process, which includes sample preparation and deciphering the test results, requires trained personnel. The entire sampling process requires at least several hours to complete and is therefore unable to handle high patient volume in a hospital setting. Given the above limitations, it appears that there is currently no available test kit that allows easy and quick differentiation of patients who are at risk of suffering spontaneous miscarriage from the group of patients presenting symptoms of miscarriage.

Given this, there remains a need for new robust sensing platforms or detection kits that allow rapid and sensitive detection of important urine metabolites, so as to identify pregnant women who have increased risk of spontaneous miscarriage. This can allow high risk patients to be identified early and quickly so that necessary treatment can be administered promptly. More importantly, these methods or kits have to be accurate, cost effective and easy to perform.

Surface-enhanced Raman scattering (SERS) is a technique that enhances the Raman scattering of molecules adsorbed on or near to the surface of plasmonic metal nanoparticles. Typically, the Raman signals of the molecules can be enhanced by several orders of magnitude due to the electromagnetic enhancement at the relevant "hot spots" on the SERS substrate. In addition to the SERS phenomenon, superhydrophobic SERS platforms can also serve as ideal platforms to further enhance the detection sensitivity by reducing the random spreading of aqueous solution (*Phys. Chem. Chem. Phys.*, 2014, 16, 26983-26990; *Anal. Chem.*, 2014, 86, 10437-10444). A superhydrophobic surface can be defined as a surface that is difficult to wet, or having a static contact angle of a water droplet exceeding 150°, with roll-off angle of less than 10°.

SUMMARY OF INVENTION

Aspects and embodiments of the current invention are provided by the following numbered clauses.

1. A composite superhydrophobic material suitable for use in surface-enhanced Raman scattering, the material comprising:
    a substrate layer comprising a set of positively or negatively charged functional groups;
    a metal nanoparticle coating on top of the substrate layer, comprising a set of negatively or positively charged functional groups;
    a metal layer on top of the metal nanoparticle coating; and
    a first superhydrophobic layer on top of the metal layer, wherein:
    the metal nanoparticle coating comprises a first set and a second set of metal nanoparticles, where the first set of metal nanoparticles has a diameter that is from 0.1 to 90% smaller than the diameter of the second set;
    the metal of the first set of metal nanoparticles is gold and/or silver;
    the metal of the second set of metal nanoparticles is gold and/or silver; and
    the charged functional groups on the substrate layer and metal nanoparticle coating are electronically complementary to one another.

2. The composite superhydrophobic material according to Clause 1, wherein the density of the metal nanoparticle coating on the surface of the substrate layer is from 2 to 20 particles/$\mu m^2$, such as from 2.5 to 10 particles/$\mu m^2$, such as from 3 to 5 particles/$\mu m^2$, such as 4.4 particles/$\mu m^2$.

3. The composite superhydrophobic material according to Clause 1 or Clause 2, wherein the composite material further comprises a second superhydrophobic layer sandwiched between the metal nanoparticle coating and the metal layer.

4. The composite superhydrophobic material according to any one of the preceding clauses, wherein the material displays a static contact angle with water of greater than 150°, such as from 151° to 170°, such as 155° to 165°.

5. The composite superhydrophobic material according to any one of the preceding clauses, wherein the first set of nanoparticles have an average diameter of from 10 to 250 nm, such as from 20 to 100 nm, such as from 30 to 50 nm, such as from 130 to 240 nm, such as from 135 to 230 nm.

6. The composite superhydrophobic material according to any one of the preceding clauses, wherein the second set of nanoparticles have an average diameter of from 250 to 1,000 nm, such as from 300 to 600 nm, such as from 311 to 540 nm.

7. The composite superhydrophobic material according to any one of the preceding clauses, wherein the first set of metal nanoparticles has a diameter that is from 0.2 to 60% smaller than the diameter of the second set, such as from 0.5 to 57% such as from 1 to 55%, such as from 10 to 50%, such as from 25 to 45% smaller than the diameter of the second set, such as from 61 to 89% smaller than the diameter of the second set, such as from 75 to 85%, such as from 79 to 83% smaller than the diameter of the second set.

8. The composite superhydrophobic material according to any one of the preceding clauses, wherein the composite has a root mean square surface roughness of from 30 to 150 nm, such as 40 to 140 nm, such as from 50 to 125 nm, such as 110 to 125 nm.

9. The composite superhydrophobic material according to any one of the preceding clauses, wherein the total number of particles in the second set of nanoparticles to the total number of particles in the first set of nanoparticles on the composite material is from 1:10 to 10:1, such as from 1:5 to 5:1, such as from 2:1 to 4:1.

10. The composite superhydrophobic material according to any one of the preceding clauses, wherein the substrate layer is formed from one or more of the group consisting of poly(dimethylsiloxane), glass and silicon.

11. The composite superhydrophobic material according to any one of the preceding clauses, wherein the set of charged functional groups on the substrate layer are positively charged and the charged functional groups on the metal nanoparticle coating are negatively charged.

12. The composite superhydrophobic material according to Clause 11, wherein the set of positively charged functional groups on the substrate layer are ammonium ions, optionally wherein the set of positively charged functional groups on the substrate layer are derived from a silane compound containing one or two amino groups, such as 3-aminopropyltriethoxysilane.

13. The composite superhydrophobic material according to Clause 11 or Clause 12, wherein the set of negatively charged functional groups on the first and second set of metal nanoparticles are carboxylate ions or alkoxide ions, optionally wherein the set of negatively charged functional groups on the first and second set of metal nanoparticles are derived from an alkylthiol containing one or more carboxylic acid groups or an alkylthiol containing one or more hydroxyl groups, such as 11-mercaptoundecanoic acid.

14. The composite superhydrophobic material according to any one of Clauses 1 to 10, wherein the set of charged functional groups on the substrate layer are negatively charged and the charged functional groups on the metal nanoparticle coating are positively charged.

15. The composite superhydrophobic material according to Clause 14, wherein the set of negatively charged functional groups on the substrate layer are carboxylate ions or alkoxide ions, optionally wherein the set of negatively charged functional groups on the substrate layer are derived from a silane compound containing one or more carboxylic acid groups or a silane compound containing one or more hydroxyl groups.

16. The composite superhydrophobic material according to Clause 14 or Clause 15, wherein the set of positively charged functional groups on the first and second set of metal nanoparticles are ammonium ions, optionally wherein the set of positively charged functional groups on the first and second set of metal nanoparticles are derived from an alkylthiol compound containing one or more amino groups.

17. The composite superhydrophobic material according to any one of the preceding clauses, wherein the metal layer is from 5 to 53 nm thick, such as from 15 to 43 nm thick, such as from 20 to 33 nm thick, such as from 25 to 30 nm thick.

18. The composite superhydrophobic material according to any one of the preceding clauses, wherein the metal layer comprises a silver layer, a gold layer or a silver and gold layer, optionally wherein the silver layer, a gold layer or a silver and gold layer is from 5 to 48 nm thick, such as from 10 to 38 nm thick, such as from 15 to 28 nm thick, such as from 20 to 25 nm thick.

19. The composite superhydrophobic material according to Clause 18, wherein the metal layer further comprises a chromium layer, optionally wherein the chromium layer is from 2 to 5 nm thick.

20. The composite superhydrophobic material according to Clause 18 or Clause 19, wherein the chromium layer is on top of the metal nanoparticle coating and the metal layer is on top of the chromium layer.

21. The composite superhydrophobic material according to any one of the preceding clauses, wherein there is direct attachment between the metal layer and the substrate layer through gaps between nanoparticles in the metal nanoparticle coating.

22. The composite superhydrophobic material according to any one of the preceding clauses, wherein the first superhydrophobic layer comprises a $C_{10}$ to $C_{20}$ thiol that is unsubstituted or substituted by one or more fluoro groups, optionally wherein the first superhydrophobic layer comprises one or more of the group consisting of 1-dodecanethiol, 1-hexadecanethiol, and 1H,1H,2H,2H-perfluorodecanethiol.

23. The composite superhydrophobic material according to any one of Clauses 3 to 22, wherein the second superhydrophobic layer comprises a $C_{10}$ to $C_{20}$ thiol that is unsubstituted or substituted by one or more fluoro groups, optionally wherein the second superhydrophobic layer comprises one or more of the group consisting of 1-dodecanethiol, 1-hexadecanethiol, and 1H,1H,2H,2H-perfluorodecanethiol.

24. The composite superhydrophobic material according to any one of the preceding clauses, wherein the first set of metal nanoparticles are nanocubes and the second set of metal nanoparticles are nanopolyhedrons having more than six faces and are selected from one or more nanopolyhedra having from 7 to 30 faces.

25. The composite superhydrophobic material according to Clause 24, wherein the second set of metal nanoparticles are nanooctahedra.

26. The composite superhydrophobic material according to any one of the preceding clauses, wherein the first and second set of nanoparticles are silver nanoparticles.

27. A kit of parts comprising:
  (ai) a composite superhydrophobic material as described in any one of Clauses 1 to 26; and
  (bi) a urine analysis formulation comprising silver and/or gold nanoparticles coated with a boronic acid comprising a thiol group, optionally wherein:
  the nanoparticles are formed from the same metal(s) used in the composite superhydrophobic material; and/or
  the boronic acid is 4-mercaptophenylboronic acid.

28. A method of predicting increased risk of spontaneous miscarriage, the method comprising the steps of:
  (a) providing an aqueous solution comprising the non-salt components of a urine sample obtained from a subject;
  (b) reacting the aqueous solution with a urine analysis formulation comprising silver and/or gold nanoparticles coated with a boronic acid comprising a thiol group for a first period of time to provide a complexed sample, optionally wherein the nanoparticles are formed from the same metal(s) used in the composite superhydrophobic material and/or the boronic acid is 4-mercaptophenylboronic acid;

(c) placing the complexed sample onto a composite superhydrophobic material as described in any one of Clauses 1 to 26 and removing the water by evaporation to provide a dried sample; and (d) subjecting the dried sample to Raman spectroscopy to determine the abundance of pregnane and tetrahydrocortisone and then predicting the risk of spontaneous miscarriage based on the formula:

$$\frac{\text{Pregnane Abundance}}{(\text{Pregnane Abundance} + \text{Tetrahydrocortisone Abundance})} \times 100\%$$

wherein a value lower than a threshold value is indicative of increased risk of spontaneous miscarriage, optionally wherein the first period of time is from 3 to 48 hours, such as 3 hours.

29. The method according to Clause 28, wherein the reaction is conducted at a pH value of from 10 to 12, such as 11.

30. The method according to Clause 29, wherein before step (c) is conducted, the reaction product of step (b) is centrifuged for a second period of time and the supernatant removed and replaced with a liquid having a pH of from 10 to 12, such as 11 and this centrifugation, supernatant removal and liquid replacement steps are repeated a further one to four times, such as a further two times.

31. The method according to any one of Clauses 28 to 30, wherein the aqueous solution provided in step (a) of the process is obtained by the following steps:
   (i) adding a urine sample comprising salt and non-salt components obtained from a subject onto a reverse phase column to provide a loaded column;
   (ii) removing the salt components from the loaded column by eluting with water, then removing and isolating the non-salt components from the loaded column by eluting with a $C_{1-4}$ alcohol (e.g. methanol) and then removing the $C_{1-4}$ alcohol; and
   (iii) adding an aqueous solution to the isolated non-salt components to provide the aqueous solution of step (a), optionally wherein the aqueous solution has a pH of from 10 to 12, such as 11.

32. The method according to any one of Clauses 28 to 31, wherein the Raman spectroscopy is conducted using a laser excitation wavelength of 532 nm, using a laser power of from 0.01 to 1 mW and an acquisition time of from 1 to 60 seconds, optionally wherein the laser power is 0.2 mW and the acquisition time is 1 second.

33. A method of making a composite superhydrophobic material suitable for use in surface-enhanced Raman scattering, the method comprising:
   (ia) providing a metal-coated composite material comprising:
      a substrate layer comprising a set of positively or negatively charged functional groups;
      a metal nanoparticle coating on top of the substrate layer, comprising a set of negatively or positively charged functional groups, where the metal nanoparticle coating comprises a first set and a second set of metal nanoparticles, where the first set of metal nanoparticles has a diameter that is from 0.1 to 90% smaller than the diameter of the second set; and
      a metal layer on top of the metal nanoparticle coating; and
   (ib) immersing the metal-coated composite material in a solution comprising a superhydrophobic material to form a superhydrophobic layer on top of the metal layer, thereby forming the composite superhydrophobic material, wherein:
   the metal of the first set of metal nanoparticles is gold and/or silver;
   the metal of the second set of metal nanoparticles is gold and/or silver; and
   the charged functional groups on the substrate layer and metal nanoparticle coating are electronically complementary to one another.

34. The method according to Clause 33, wherein the metal-coated composite material is formed by:
   (A) providing a metal nanoparticle coated substrate comprising a substrate layer that comprises a set of positively or negatively charged functional groups and a metal nanoparticle coating on top of the substrate layer that comprises a set of negatively or positively charged functional groups, where the metal nanoparticle coating comprises a first set and a second set of metal nanoparticles; and
   (B) depositing a metal layer on top of the metal nanoparticle coated substrate, optionally wherein the deposition is by thin-film deposition by thermal evaporation of a metal.

35. The method according to Clause 34, wherein the metal-coated composite material comprises a further superhydrophobic layer sandwiched between the metal nanoparticle coating and the metal layer.

36. The method according to Clause 35, wherein the further superhydrophobic layer is formed by immersing a metal nanoparticle coated substrate in a solution comprising a superhydrophobic material to form a superhydrophobic layer on top of the metal nanoparticle layer, where the metal nanoparticle coated substrate comprises a substrate layer that comprises a set of positively or negatively charged functional groups and a metal nanoparticle coating on top of the substrate layer that comprises a set of negatively or positively charged functional groups, where the metal nanoparticle coating comprises a first set and a second set of metal nanoparticles.

37. The method according to any one of Clauses 33 to 36, wherein the metal layer is from 5 to 53 nm thick, such as from 15 to 43 nm thick, such as from 20 to 33 nm thick, such as from 25 to 30 nm thick.

38. The method according to any one of Clauses 33 to 37, wherein the metal layer comprises a silver layer, a gold layer or a silver and gold layer, optionally wherein the silver layer, gold layer or silver and gold layer is from 5 to 48 nm thick, such as from 10 to 38 nm thick, such as from 15 to 28 nm thick, such as from 20 to 25 nm thick.

39. The method according to Clause 38, wherein the metal layer further comprises a chromium layer, optionally wherein the chromium layer is from 2 to 5 nm thick.

40. The method according to Clause 38 or Clause 39, wherein the chromium layer is on top of the metal nanoparticle layer and the silver layer, gold layer or silver and gold layer is on top of the chromium layer.

41. The method according to any one of Clauses 33 to 40, wherein the metal nanoparticle coated substrate is formed by contacting a substrate comprising a set of positively or negatively charged functional groups with a solution comprising metal nanoparticles comprising a set of negatively or positively charged functional groups, where the metal nanoparticles comprise a first and second set of metal nanoparticles.

42. The method according to any one of Clauses 33 to 41, wherein the first set of nanoparticles have an average diameter of from 10 to 250 nm, such as from 20 to 100 nm, such as from 30 to 50 nm, such as from 130 to 240 nm, such as from 135 to 230 nm.

43. The method according to any one of Clauses 33 to 42, wherein the second set of nanoparticles have an average diameter of from 250 to 1,000 nm, such as from 300 to 600 nm, such as from 311 to 540 nm.

44. The method according to any one of Clauses 33 to 43, wherein the first set of metal nanoparticles has a diameter that is from 0.2 to 60% smaller than the diameter of the second set, such as from 0.5 to 57% such as from 1 to 55%, such as from 10 to 50%, such as from 25 to 45% smaller than the diameter of the second set, such as from 61 to 89% smaller than the diameter of the second set, such as from 75 to 85%, such as from 79 to 83% smaller than the diameter of the second set.

45. The method according to any one of Clauses 33 to 44, wherein the composite has a root mean square surface roughness of from 30 to 150 nm, such as 40 to 140 nm, such as from 50 to 125 nm, such as 110 to 125 nm.

46. The method according to any one of Clauses 33 to 45, wherein the total number of particles in the second set of nanoparticles to the total number of particles in the first set of nanoparticles on the composite material is from 1:10 to 10:1, such as from 1:5 to 5:1, such as from 2:1 to 4:1.

47. The method according to any one of Clauses 33 to 46, wherein the substrate is one or more of the group consisting of poly(dimethylsiloxane), glass and silicon.

48. The method according to any one of Clauses 33 to 47, wherein the set of charged functional groups on the substrate layer are positively charged and the charged functional groups on the metal nanoparticle coating are negatively charged.

49. The method according to Clause 48, wherein the set of positively charged functional groups on the substrate layer are ammonium ions, optionally wherein the set of positively charged functional groups on the substrate layer are derived from a silane compound containing one or two amino groups, such as 3-aminopropyltriethoxysilane.

50. The method according to Clause 48 or Clause 49, wherein the set of negatively charged functional groups on the first and second set of metal nanoparticles are carboxylate ions or alkoxide ions, optionally wherein the set of negatively charged functional groups on the first and second set of metal nanoparticles are derived from an alkylthiol containing one or more carboxylic acid groups or an alkylthiol containing one or more hydroxyl groups, such as 11-mercaptoundecanoic acid.

51. The method according to any one of Clauses 33 to 47, wherein the set of charged functional groups on the substrate layer are negatively charged and the charged functional groups on the metal nanoparticle coating are positively charged.

52. The method according to Clause 51, wherein the set of negatively charged functional groups on the substrate layer are carboxylate ions or alkoxide ions, optionally wherein the set of negatively charged functional groups on the substrate layer are derived from a silane compound containing one or more carboxylic acid groups or a silane compound containing one or more hydroxyl groups.

53. The method according to Clause 51 or Clause 52, wherein the set of positively charged functional groups on the first and second set of metal nanoparticles are ammonium ions, optionally wherein the set of positively charged functional groups on the first and second set of metal nanoparticles are derived from an alkylthiol compound containing one or more amino groups.

54. The method according to any one of Clauses 33 to 53, wherein the superhydrophobic material used in step (ib) of Clause 33 is a $C_{10}$ to $C_{20}$ thiol that is unsubstituted or substituted by one or more fluoro groups, optionally wherein the superhydrophobic material is selected from one or more of the group consisting of 1-dodecanethiol, 1-hexadecanethiol, and 1H,1H,2H,2H-perfluorodecanethiol.

55. The method according to any one of Clauses 35 to 54, wherein the superhydrophobic material used to form the further superhydrophobic layer is a $C_{10}$ to $C_{20}$ thiol that is unsubstituted or substituted by one or more fluoro groups, optionally wherein the superhydrophobic material is selected from one or more of the group consisting of 1-dodecanethiol, 1-hexadecanethiol, and 1H,1H,2H,2H-perfluorodecanethiol.

56. The method according to any one of Clauses 33 to 55, wherein the first set of metal nanoparticles are nanocubes and the second set of metal nanoparticles are nanopolyhedrons having more than six faces and are selected from one or more nanopolyhedra having from 7 to 30 faces.

57. The method according to Clause 56, wherein the second set of metal nanoparticles are nanooctahedra.

58. The method according to any one of Clauses 33 to 57, wherein the first and second set of nanoparticles are silver nanoparticles.

(e, f) static contact angle of the hydrophilic and superhydrophobic substrate 109, respectively; (g) optical image of a spot area of a dried sample on the hydrophilic substrate; (h) SEM image of a dried sample on substrate 109.

Figure 9:
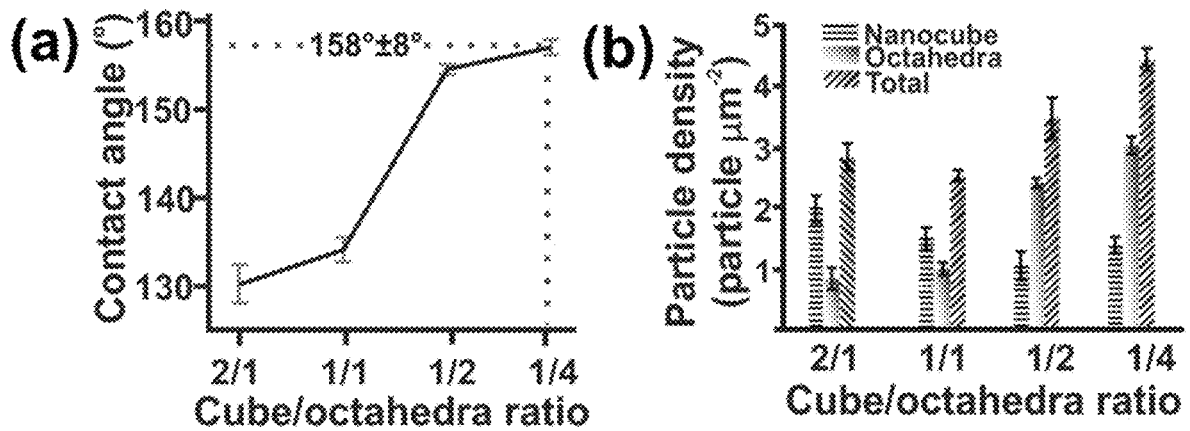

FIG. 9 Depicts the effect of particle ratio of AgNC to AgNO on: (a) the static contact angles; and (b) particle density of the superhydrophobic substrate 109.

Figure 10:
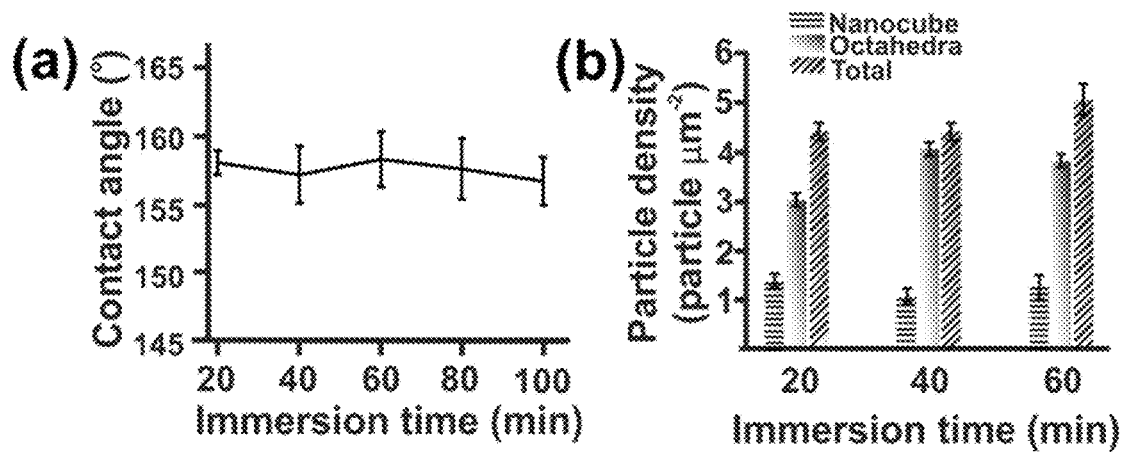

FIG. 10 Depicts the effect of incubation time of substrate 80 in the Ag nanoparticle mixture (AgNC and AgNO) on: (a) the static contact angles; and (b) particle density of the superhydrophobic substrate 109.

Figure 11:
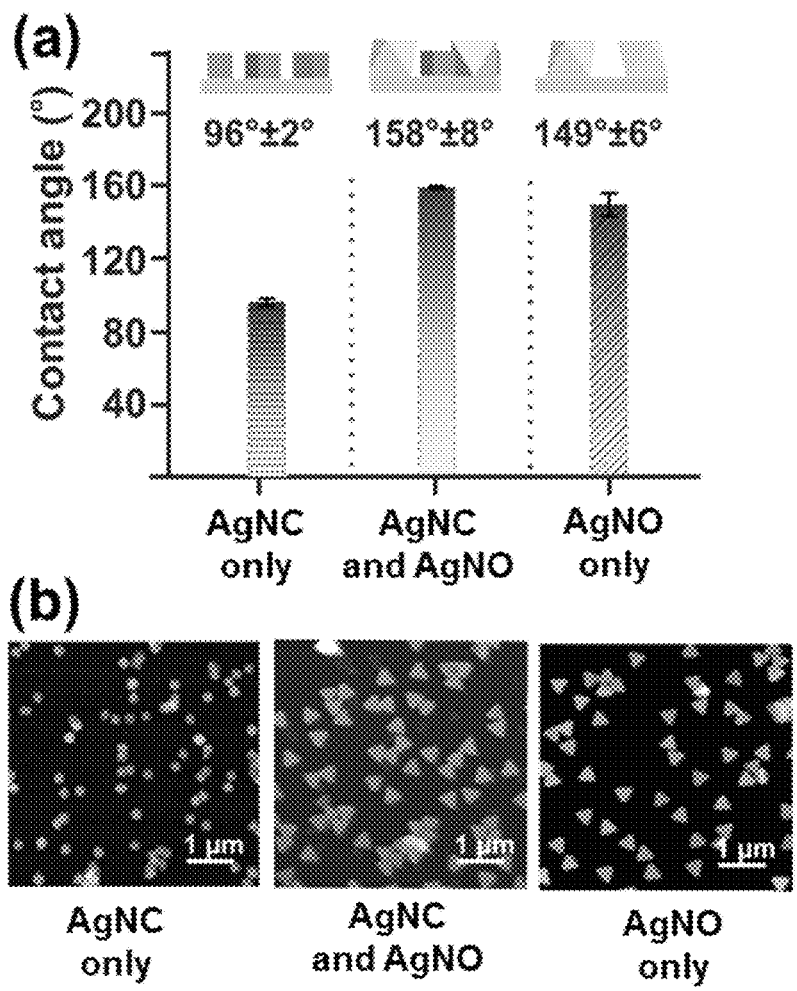

FIG. 11 Depicts: (a) the effect of having AgNC or AgNO alone, and a binary assembly of AgNC and AgNO on the static contact angles of the superiydrophobic substrate 109; and (b) the AFM images of the respective substrates.

Figure 12:
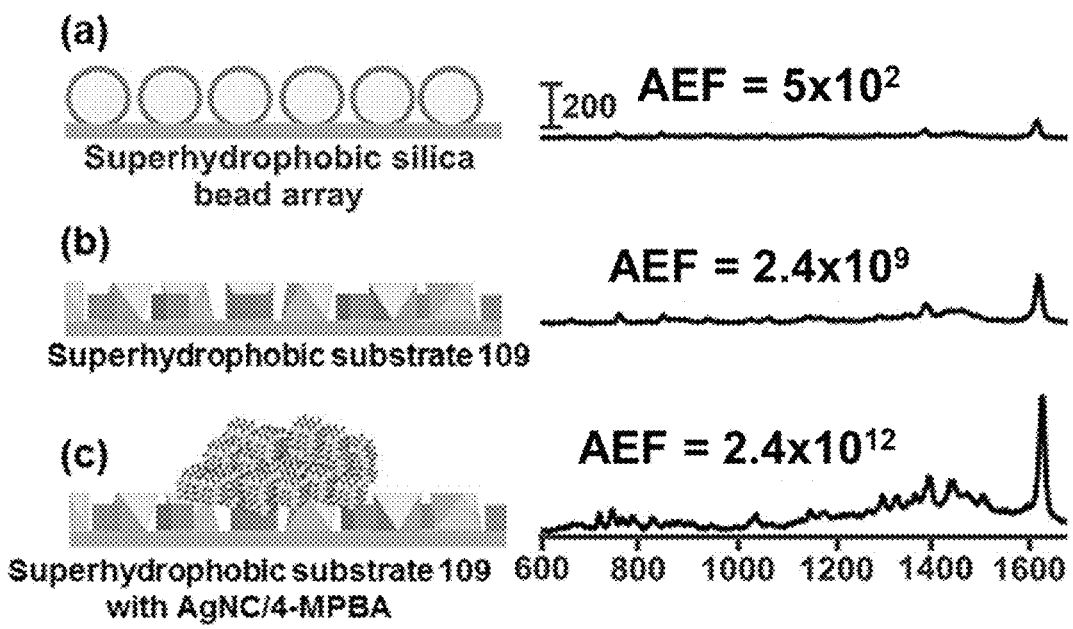

FIG. 12 Depicts the SERS spectra of methylene blue and the corresponding analytical enhancement factor (AEF) of: (a) superhydrophobic silica bead array; (b) superhydrophobic substrate 109; and (c) superhydrophobic substrate 109 with AgNC/4-MPBA.

Figure 13C:
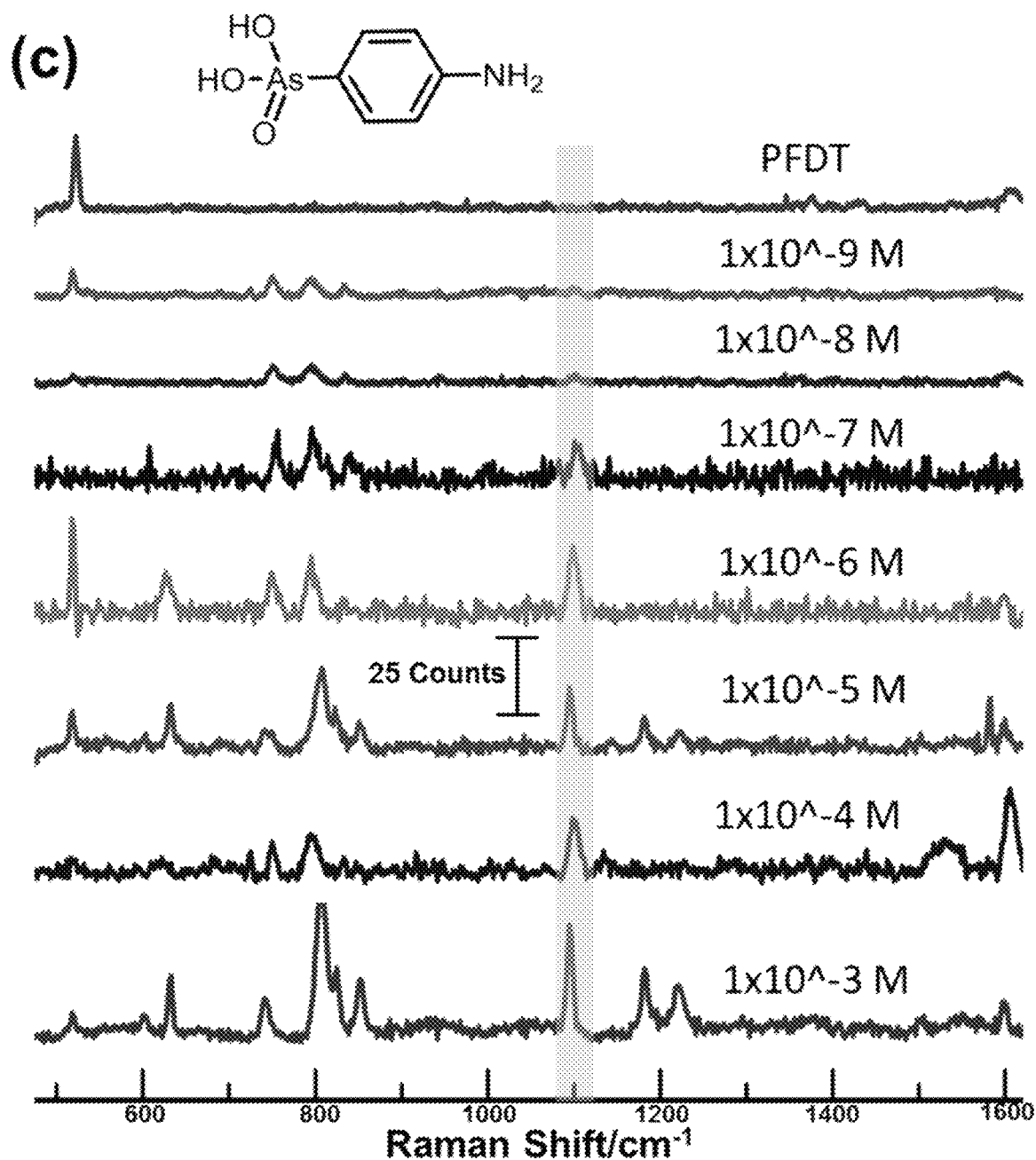
Figure 13D:
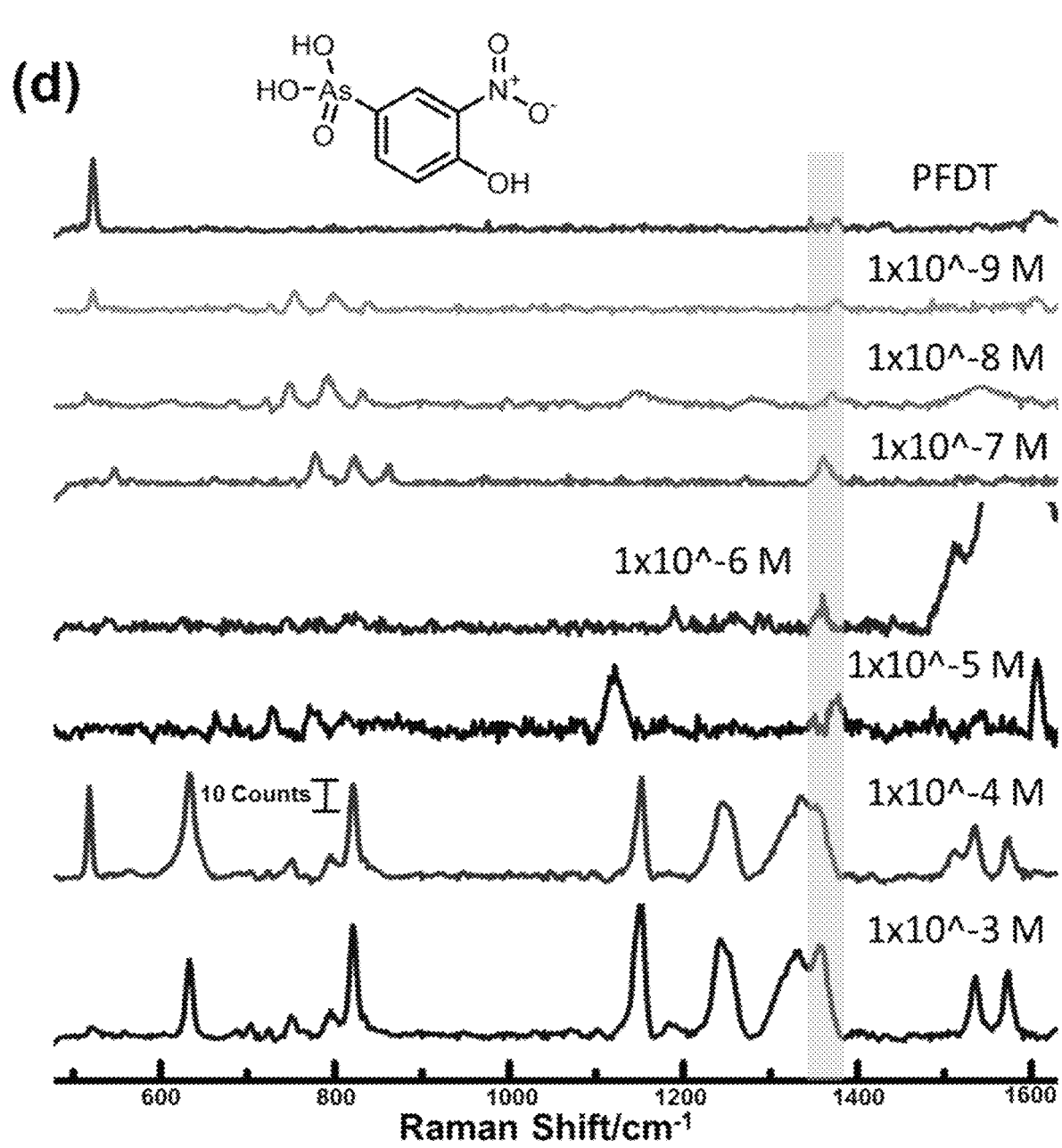

FIG. 13 Depicts the use of the initial batch of superhydrophobic substrate 107 to detect urine metabolites and toxins: (a, b) show the SERS spectra of 5β-pregnane-3α, 20α-diol glucuronide (pregnane) at various concentrations, and a calibration curve of the signal intensity as a function of concentration, respectively; (c, d) show the SERS spectra of p-arsanilic acid and roxarsone, respectively, at various concentrations.

Figure 14:
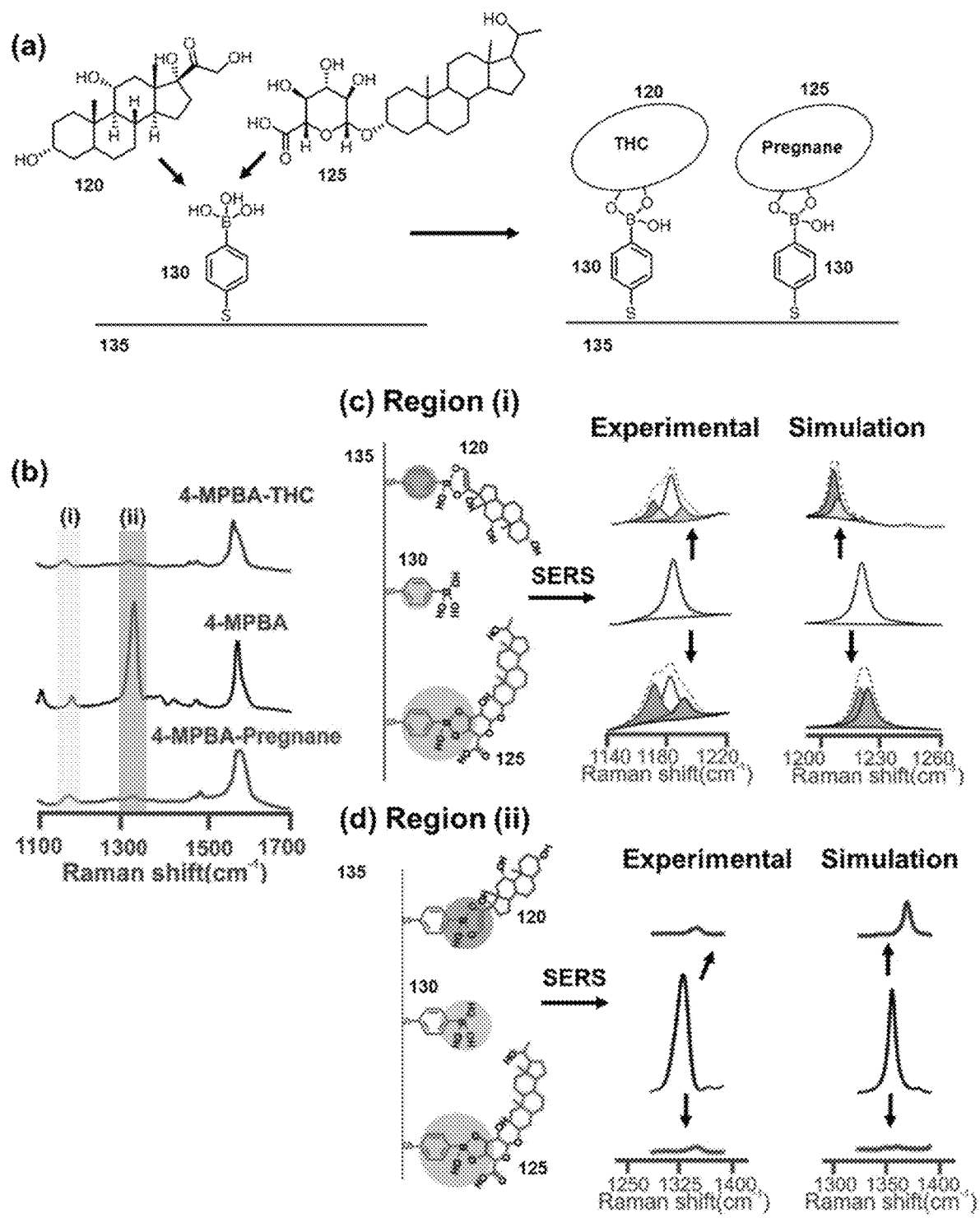

FIG. 14 Depicts: (a) a schematic representation of the binding of THC (120) and pregnane (125) onto 4-MPBA (130) anchored onto AgNC surface 135; (b) SERS spectra of 4-MPBA, 4-MPBA after incubation with THC and pregnane respectively, using AgNC/4-MPBA with the superhydrophobic substrate 109; the experimental and simulated SERS spectra in (c) Region (i); and (d) Region (ii) of the spectra of 4-MPBA upon binding to THC (120) and pregnane (125).

Figure 15:
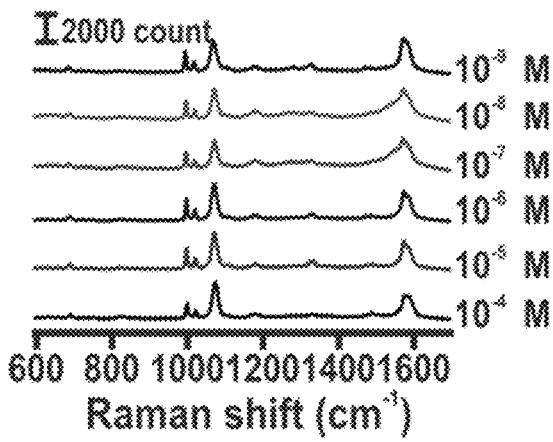
Figure 15:
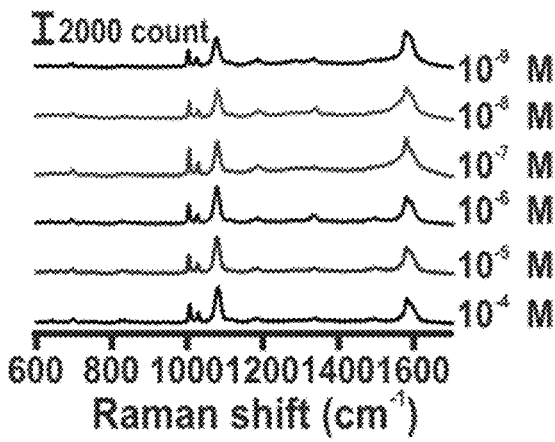
Figure 15:
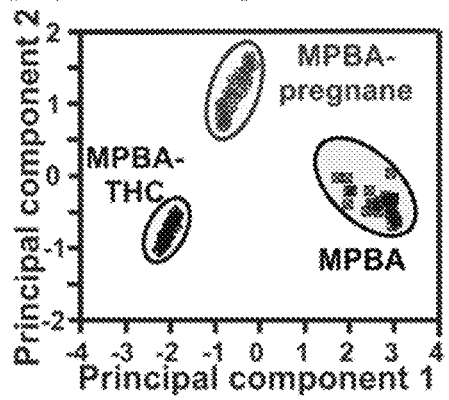
Figure 15:
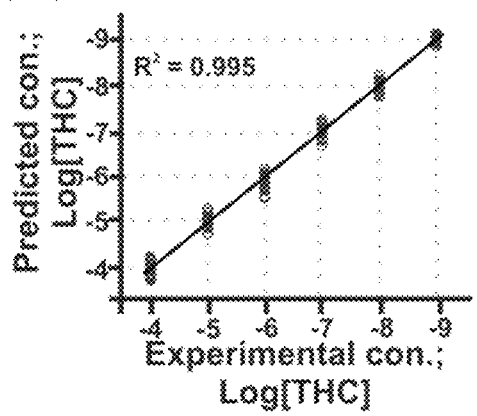
Figure 15:
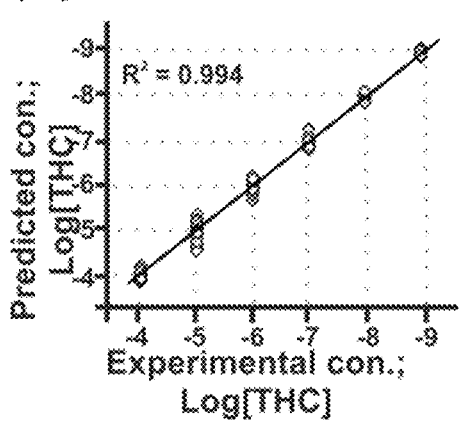
Figure 15:
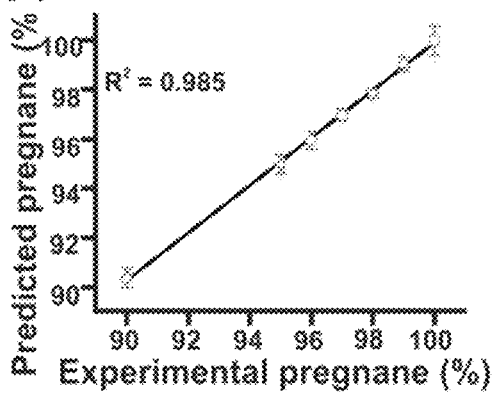

FIG. 15 Depicts: (a, b) the SERS spectra of AgNC/4-MPBA after incubating with pregnane and THC respectively, at different concentrations from $10^{-4}$-$10^{-9}$ M on the superhydrophobic substrate 109; (c) PCA clustering of the respective SERS spectra relating to AgNC/4-MPBA, and after incubating with pregnane and THC respectively; (d, e) PLS concentration prediction model of the pregnane and THC, respectively, from $10^{-4}$-$10^{-9}$ M; and (f) PLS model of a mixture of pregnane and THC at different pregnane percentage.

Figure 16:
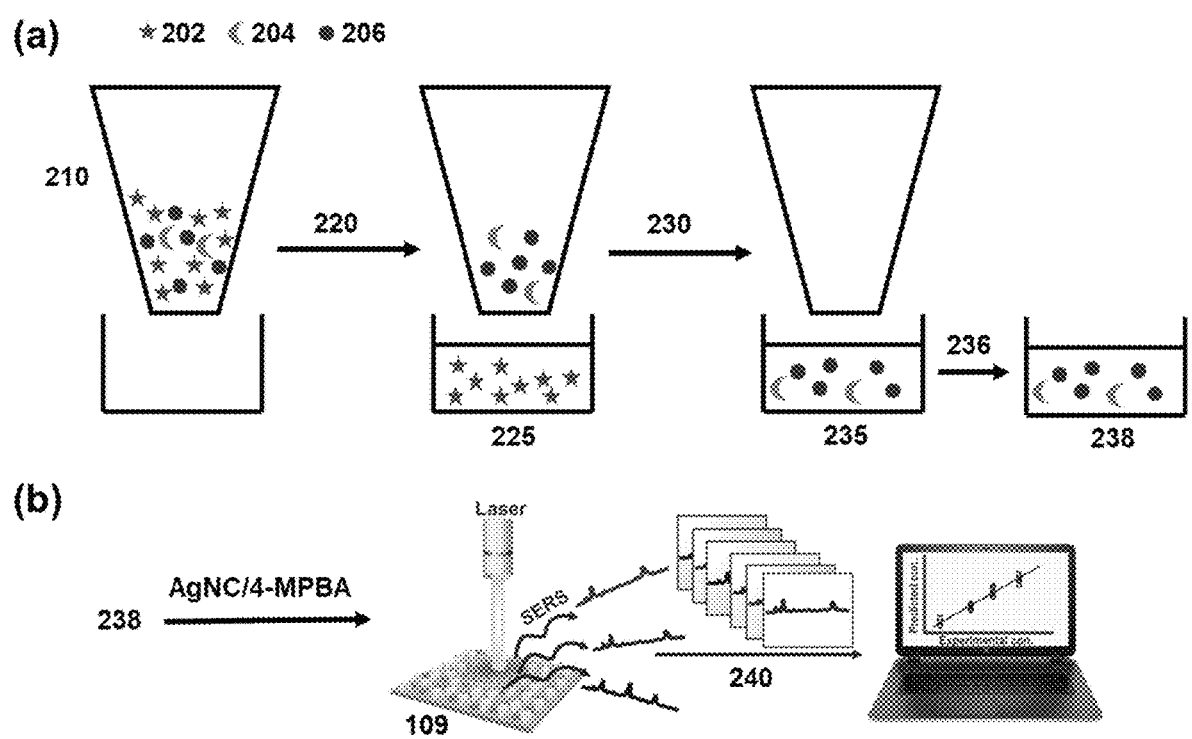

FIG. 16 Depicts: (a) a schematic representation of the ZIPTIP pre-treatment of artificial or real urine samples; (b) a schematic representation of subjecting the treated sample 238 with AgNC/4-MPBA, followed by SERS detection on the superhydrophobic substrate 109 and chemometric analysis 240.

Figure 17:
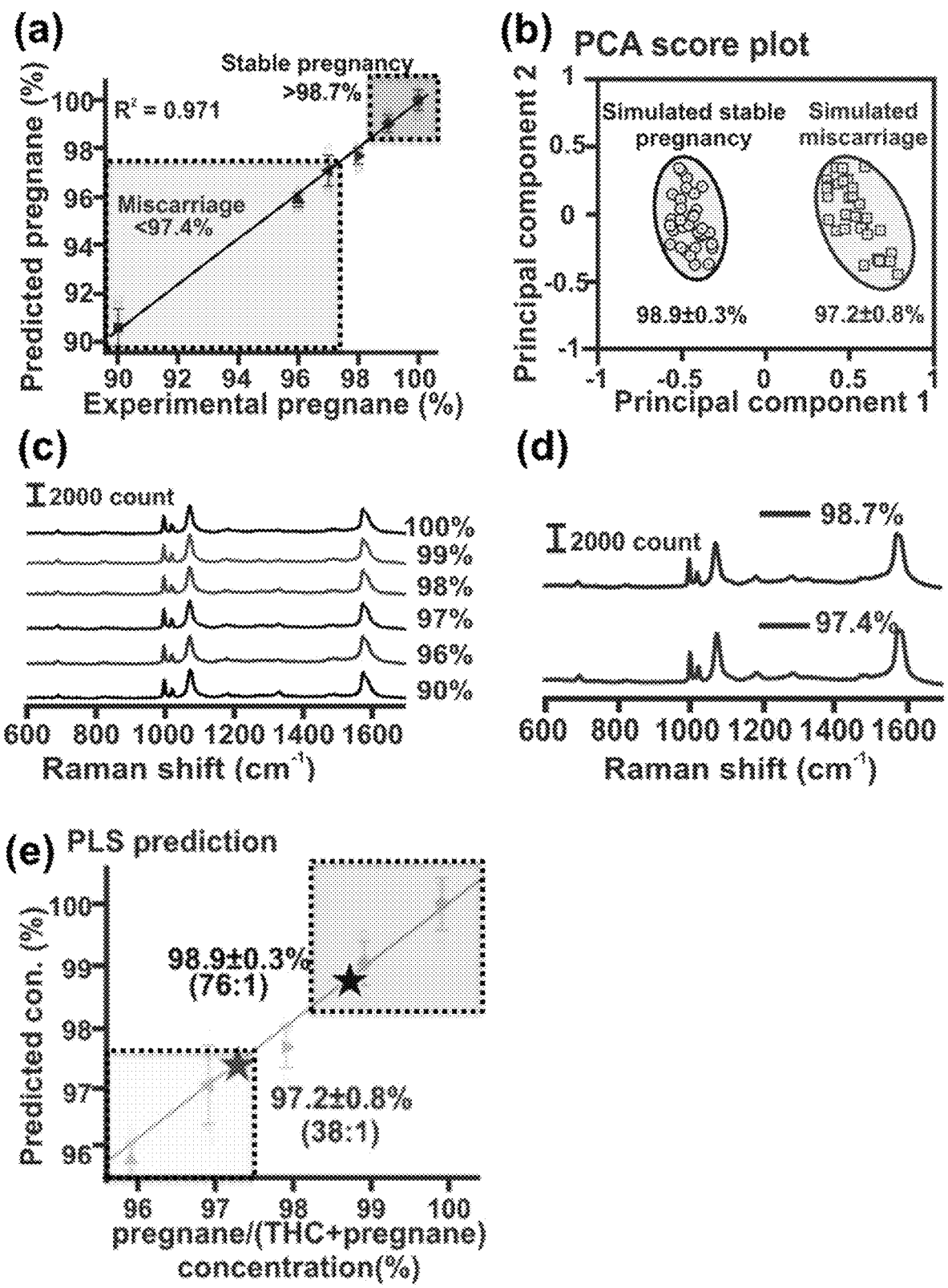

FIG. 17 Depicts: (a) the PLS prediction model prepared using various concentrations of pregnane in artificial urine; (b) PCA clustering of the SERS spectra obtained from artificial urine samples that simulate stable pregnancy (98.7% of pregnane) and from urine samples that simulate miscarriage (97.4% of pregnane); (c) SERS spectra relating to AgNC/4-MPBA, after incubating with the artificial urine samples, with various concentrations of pregnane; (d) SERS spectra relating to AgNC/4-MPBA, after incubating with the artificial urine samples spiked with 98.7% pregnane (to simulate stable pregnancy) and with 97.4% pregnane (to simulate risk of miscarriage), respectively; and (e) the PLS model established using various concentrations of pregnane in artificial urine, fitted with two points (stars) that represent simulated stable pregnancy and simulated miscarriage respectively.

Figure 18:
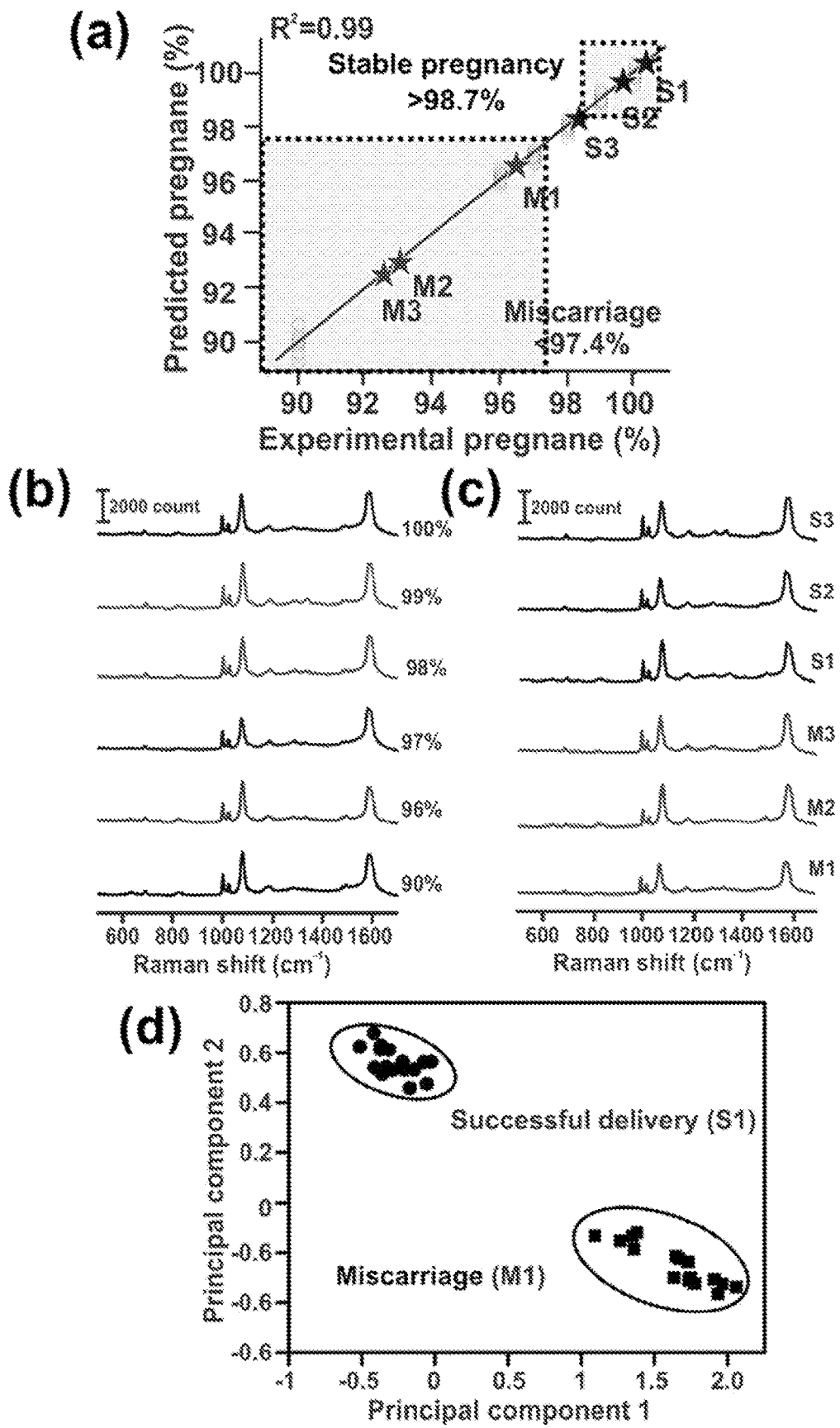

FIG. 18 Depicts: (a) the PLS prediction model prepared using various concentrations of pregnane in real urine samples of non-pregnant women. The prediction plot was fitted with points (stars) corresponding to individuals with successfully delivery (S1-S3) and with miscarriage (M1-M3); (b) SERS spectra of real urine samples of non-pregnant women spiked with different concentrations of pregnane; (c) SERS spectra of actual urine samples from pregnant women, corresponding to those with successful delivery (S1-S3) and miscarriage (M1-M3); and (d) PCA clustering of the SERS spectra obtained from actual samples from pregnant women with successful delivery (S1) and with miscarriage (M1).

Figure 19:
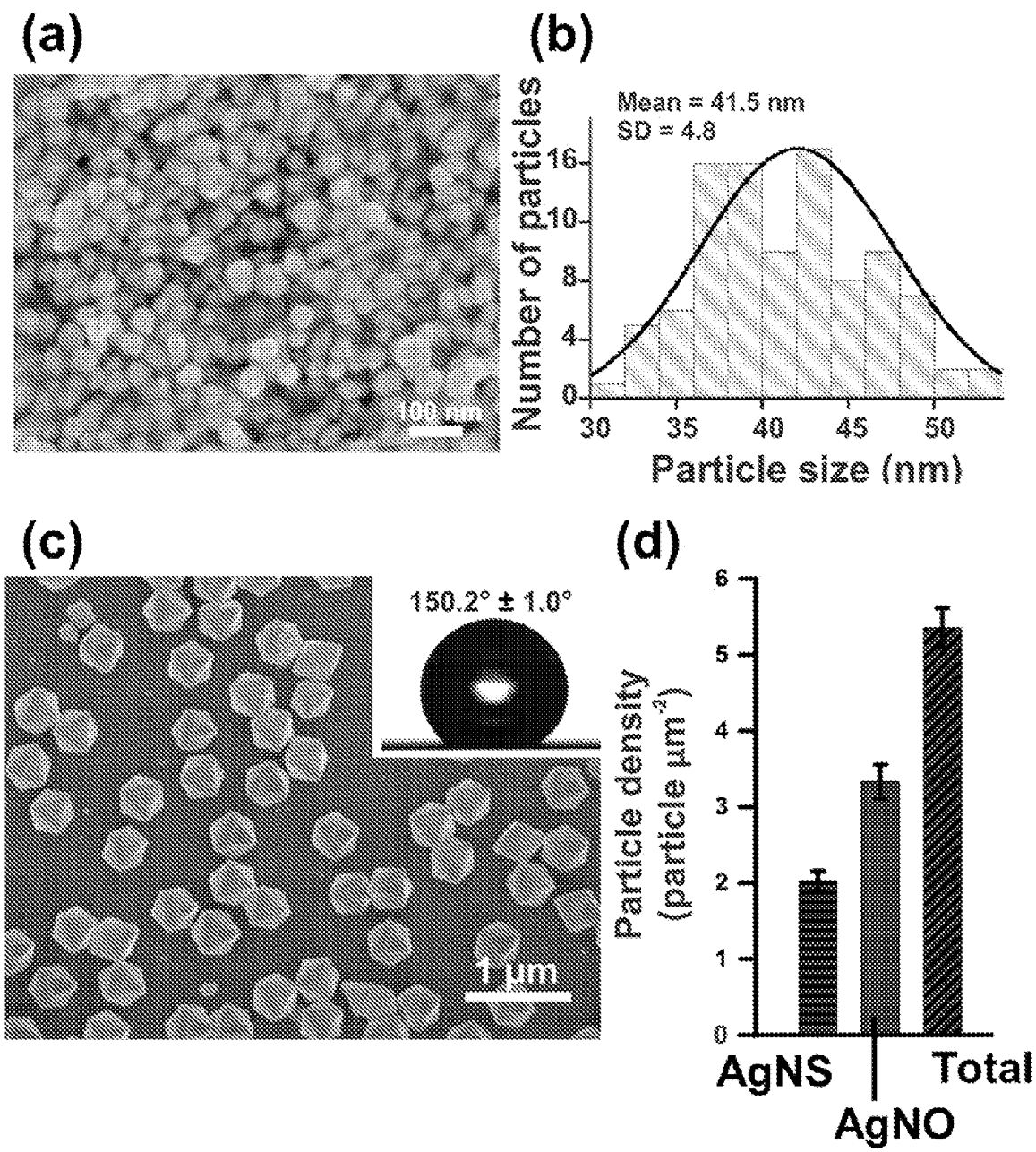

FIG. 19 Depicts: (a, b) the SEM image and particle size distribution of AgNS, respectively; (c) the SEM image and static contact angle; and (d) particle density of a superhydrophobic substrate containing a binary assembly of AgNS and AgNO.

DESCRIPTION

As noted hereinbefore, the current invention relates to a composite superhydrophobic material suitable for use in surface-enhanced Raman scattering, the material comprising:
a substrate layer comprising a set of positively or negatively charged functional groups;
a metal nanoparticle coating on top of the substrate layer, comprising a set of negatively or positively charged functional groups;
a metal layer on top of the metal nanoparticle coating; and
a first superhydrophobic layer on top of the metal layer, wherein:
the metal nanoparticle coating comprises a first set and a second set of metal nanoparticles, where the first set of metal nanoparticles has a diameter that is from 0.1 to 90% smaller than the diameter of the second set;
the metal of the first set of metal nanoparticles is gold and/or silver;
the metal of the second set of metal nanoparticles is gold and/or silver; and
the charged functional groups on the substrate layer and metal nanoparticle coating are electronically complementary to one another.

When used herein, the terms "superhydrophobic" refers to a material that has one or more surfaces that are highly hydrophobic, making these surfaces extremely difficult to wet. For example, a superhydrophobic material mentioned herein may be a material which has one or more surfaces that display a static contact angle with water of greater than 150°. Examples of suitable static contact angles with water that may be mentioned herein include, but are not limited to, a contact angle of from 151° to 170°, such as 155° to 165°. Details of the static contact angle measurement technique are provided in the examples section below.

For the avoidance of doubt, when numerical values are presented in the current application, any suitable combination of the end-points is explicitly contemplated herein. For example, the following contact angle ranges are contemplated:
greater than 150°, from greater than 150° to 151°, from greater than 150° to 155°, from greater than 150° to 165°, from greater than 150° to 170°;
from 151° to 155°, from 151° to 165°, from 151° to 170°; and from 155° to 165°, from 155° to 170°.

Surface-enhanced Raman scattering (SERS) is a surface-sensitive technique that enhances Raman scattering by molecules adsorbed on rough metal surfaces or by nanostructures on a surface. Thus, the resulting composite materials discussed herein may have a suitably rough surface that enables SERS analysis. For example, the composite material may have a root mean square roughness value of from 30 to 150 nm, such as 40 to 140 nm, such as from 50 to 125 nm, such as 110 to 125 nm.

When used herein, the term "substrate" refers to any suitable base material that is suitable for functionalisation with positive or negative functional groups. Examples of suitable substrates include, but are not limited to selenium, poly(dimethylsiloxane), silicon, glass, plastic, and the like. Said substrates may be presented in any suitable planar form, such as a chip or wafer. Details of how such substrates can be functionalised to present a charged surface is provided below.

When used herein, the term "positively charged functional group" refers to a functional group that carries a positive charge under suitable conditions. Examples of suitable functional groups include, but are not limited to amino functional groups (e.g. in the form of ammonium groups) and the like.

When used herein, the term "negatively charged functional group" refers to a functional group that carries a negative charge under suitable conditions. Examples of suitable functional groups include, but are not limited to carboxylic acid and alcohol functional groups (e.g. in the form of carboxylate groups and alkoxide), sulfonic acid, nucleic acid, and the like.

The term "metal nanoparticle" is intended herein to refer to gold nanoparticles, silver nanoparticles, alloys of gold and silver and any suitable combination thereof.

As noted above, the metal nanoparticle coating on top of the substrate layer has a charge that is opposite to that of the substrate layer. For example, if the substrate is positively charged, then the metal nanoparticle coating contains metal nanoparticles that are negatively charged and vice versa. Given this, an electrostatic attraction is formed between the substrate and the metal nanoparticles, which enables the formation of the coating layer.

The metal nanoparticle coating layer is formed by two differently-sized sets of metal nanoparticles deposited on the surface of the substrate. As indicated, the first set of metal nanoparticles have a diameter that is from 0.1 to 90% smaller than the diameter of the second set. For example, the first set of metal nanoparticles may have a diameter that is from 0.2 to 60% smaller than the diameter of the second set, such as from 0.5 to 57% such as from 1 to 55%, such as from 10 to 50%, such as from 25 to 45% smaller than the diameter of the second set. In alternative embodiments, the first set of metal nanoparticles may have a diameter that is from 61 to 89% smaller than the diameter of the second set, such as from 75 to 85%, such as from 79 to 83% smaller than the diameter of the second set. For the avoidance of doubt, it is specifically contemplated that all numerical values stated above may be combined to provide suitable ranges. For example, the above values also disclose ranges of from 0.2 to 89%, from 0.5 to 89% and from 0.5 to 83% etcetera.

In certain embodiments that may be mentioned herein, the first set of nanoparticles may have an average diameter of from 10 to 250 nm, such as from 20 to 100 nm, such as from 30 to 50 nm, or such as from 130 to 240 nm, such as from 135 to 230 nm; and/or the second set of nanoparticles have an average diameter of from 250 to 1,000 nm, such as from 300 to 600 nm, such as from 311 to 540 nm. As will be appreciated, these ranges may be combined in any suitable manner. For example, when the first set of nanoparticles have an average diameter of from 130 to 250 nm, then the second set of nanoparticles may have a diameter selected from the following ranges: 250 to 300 nm, 250 to 311 nm, 250 to 540 nm, 250 to 600 nm and 250 to 1,000 nm. In the situation where the first set of nanoparticles have a diameter of 250 nm, then the lower limit of the second set of nanoparticles is adjusted accordingly to be at least 0.1% larger (i.e. at least approximately 250.25 nm in diameter).

Any suitable ratio of the first and second sets of nanoparticles may be used. For example, in embodiments of the invention that may be mentioned herein, the total number of particles in the second set of nanoparticles to the total number of particles in the first set of nanoparticles on the composite material may be from 1:10 to 10:1, such as from 1:5 to 5:1, such as from 2:1 to 4:1.

The first and second set of metal nanoparticles may have any suitable shape. For example, the first and second set of metal nanoparticles may have a spheroidal shape or a polyhedral shape. Examples of suitable polyhedral shapes include cubes and polyhedrons having more than six faces, such as polyhedrons having from 7 to 30 faces. The first and second set of metal nanoparticles may have the same shape (thus differentiated only by size) or have a different shape (thus differentiated both by size and shape). In certain embodiments that may be mentioned herein, the first set of metal nanoparticles may be nanocubes and the second set of metal nanoparticles may be nanopolyhedrons having more than six faces that may be selected from one or more nanopolyhedra having from 7 to 30 faces (e.g. the second set of metal nanoparticles may be nanooctahedra).

The metal nanoparticle layer is composed of individual nanoparticles that are electrostatically bound to the surface of the substrate layer by charge attraction between the respective sets of charged functional groups on the surface of the metal nanoparticles and the substrate.

In certain embodiments, the set of charged functional groups on the substrate layer may be positively charged and the charged functional groups on the metal nanoparticle coating may be negatively charged. When the functional groups on the substrate layer are positively charged, they may be ammonium ions. Any suitable ligand capable of bonding to the substrate and providing ammonium ions may be used for this purpose. For example, the set of positively charged functional groups on the substrate layer may be derived from a silane compound containing one or two amino groups, such as 3-aminopropyltriethoxysilane. When the functional groups on the first and second set of metal nanoparticles are negatively charged they may be carboxylate ions or alkoxide ions. Any suitable ligand capable of bonding to the metal and providing carboxylate or hydroxide ions may be used for this purpose. For example, the set of negatively charged functional groups on the first and second set of metal nanoparticles may be derived from an alkylthiol containing one or more carboxylic acid groups or an alkylthiol containing one or more hydroxyl groups, such as 11-mercaptoundecanoic acid.

In certain embodiments, the set of charged functional groups on the substrate layer may be negatively charged and the charged functional groups on the metal nanoparticle coating may be positively charged. When the functional groups on the substrate layer are negatively charged, they may be carboxylate ions or alkoxide ions. Any suitable ligand capable of bonding to the substrate and providing carboxylate or alkoxide ions may be used for this purpose. For example, the set of negatively charged functional groups on the substrate layer may be derived from a silane compound containing one or more carboxylic acid groups or a silane compound containing one or more hydroxyl groups. When the functional groups on the first and second set of metal nanoparticles are positively charged they may be ammonium ions. Any suitable ligand capable of bonding to the metal and providing ammonium ions may be used for this purpose. For example, the set of positively charged functional groups on the first and second set of metal nanoparticles may be derived from an alkylthiol compound containing one or more amino groups.

The metal nanoparticle coating on the surface of the substrate layer may have a density of from 2 to 20 particles/$\mu m^2$, such as from 2.5 to 10 particles/$\mu m^2$, such as from 3 to 5 particles/$\mu m^2$, such as 4.4 particles/$\mu m^2$. As will be appreciated, the above densities may result in gaps existing between neighbouring metal nanoparticles, which may expose parts of the surface of the substrate for interaction with layers placed on top of the metal nanoparticle coating layer. For example, the gaps in the metal nanoparticle coating may allow direct attachment of the metal layer placed on top of the metal nanoparticle coating with the substrate layer through said gaps, thereby locking the metal nanoparticles in place on the surface of the substrate through physical constraint, as well as through the electrostatic interaction between the positively and negatively charged functional groups on the metal nanoparticles and the substrate.

The metal layer may be from 5 to 53 nm thick, such as from 15 to 43 nm thick, such as from 20 to 33 nm thick, such as from 25 to 30 nm thick. The metal layer may be a silver layer, a gold layer or a silver and gold layer, which may be from 5 to 48 nm thick, such as from 10 to 38 nm thick, such as from 15 to 28 nm thick, such as from 20 to 25 nm thick. In certain embodiments, the metal layer may further contain a chromium layer, which may be from 2 to 5 nm thick. When present, the chromium layer may be directly on top of the metal nanoparticle coating, with the rest of the metal layer (i.e. silver, gold or silver and gold layer) being on top of the chromium layer.

The first superhydrophobic layer may use any suitable superhydrophobic material or combination thereof. Examples of suitable superhydrophobic materials include, but is not limited to, a $C_{10}$ to $C_{20}$ thiol that is unsubstituted or substituted by one or more fluoro groups.

For example, the first superhydrophobic layer may be formed from one or more of the group consisting of 1-dodecanethiol, 1-hexadecanethiol, and 1H,1H,2H,2H-perfluorodecanethiol.

In certain embodiments of the invention, a second superhydrophobic layer sandwiched between the metal nanoparticle coating and the metal layer. Without wishing to be bound by theory, the second hydrophobic layer replaces the charged functional groups on the exposed surface of the metal nanoparticles, therefore providing a cleaner SERS substrate background spectrum. The second superhydrophobic layer may be formed from the same materials as the first superhydrophobic layer.

In embodiments of the invention, the metal nanoparticles and the metal layer may be selected from silver, gold or combinations/alloys thereof. While any suitable combination is possible, in particular embodiments mentioned herein, the metal nanoparticles and metal layer may be formed from silver (with the metal layer optionally being formed from a layer of chromium and a layer of silver).

The composite superhydrophobic material suitable for use in surface-enhanced Raman scattering may be manufactured by a method comprising:

(ia) providing a metal-coated composite material comprising:
  a substrate layer comprising a set of positively or negatively charged functional groups;
  a metal nanoparticle coating on top of the substrate layer, comprising a set of negatively or positively charged functional groups, where the metal nanoparticle coating comprises a first set and a second set of metal nanoparticles, where the first set of metal nanoparticles has a diameter that is from 0.1 to 90% smaller than the diameter of the second set; and
  a metal layer on top of the metal nanoparticle coating; and (ib) immersing the metal-coated composite material in a solution comprising a superhydrophobic material to form a superhydrophobic layer on top of the metal layer, thereby forming the composite superhydrophobic material, wherein:
  the metal of the first set of metal nanoparticles is gold and/or silver;
  the metal of the second set of metal nanoparticles is gold and/or silver; and the charged functional groups on the substrate layer and metal nanoparticle coating are electronically complementary to one another.

As will be appreciated, the resulting components and dimensions of the composite superhydrophobic material made by the above method are identical to those described above and so will now be described herein with relation to the method.

The metal-coated composite material may be formed by:
(A) providing a metal nanoparticle coated substrate comprising a substrate layer that comprises a set of positively or negatively charged functional groups and a metal nanoparticle coating on top of the substrate layer that comprises a set of negatively or positively charged functional groups, where the metal nanoparticle coating comprises a first set and a second set of metal nanoparticles; and
(B) depositing a metal layer on top of the metal nanoparticle coated substrate, optionally wherein the deposition is by thin-film deposition by thermal evaporation of a metal.

Details of the metal layer and the metal nanoparticles are described above in relation to the composite superhydrophobic material product.

In certain embodiments, the metal-coated composite material may comprise a further superhydrophobic layer sandwiched between the metal nanoparticle coating and the metal layer. In embodiments where this further superhydrophobic layer is present, it may be formed by immersing a metal nanoparticles coated substrate in a solution comprising a superhydrophobic material to form a superhydrophobic layer on top of the metal nanoparticle layer, where the metal nanoparticle coated substrate comprises a substrate layer that comprises a set of positively or negatively charged functional groups and a metal nanoparticle coating on top of the substrate layer that comprises a set of negatively or positively charged functional groups, where the metal nanoparticle coating comprises a first set and a second set of metal nanoparticles.

The metal nanoparticle coated substrate may be formed by contacting a substrate comprising a set of positively or negatively charged functional groups with a solution comprising metal nanoparticles, which comprise a set of negatively or positively charged functional groups, where the metal nanoparticles comprise a first and second set of metal nanoparticles. Said first and second sets of metal nanoparticles are described above in relation to the composite superhydrophobic material product.

While the use of the composite superhydrophobic material described above alone can improve SERS detection of analytes in a sample, it is especially effective when used in combination with metal nanoparticles that can be added directly to a processed sample of urine. Thus, the invention also includes a kit of parts comprising:
(ai) a composite superhydrophobic material as described above; and
(bi) a urine analysis formulation comprising silver and/or gold nanoparticles coated with a boronic acid comprising a thiol group.

As will be appreciated, the use of the composite superhydrophobic material alone can allow the SERS detection and quantification of the analytes directly. That is, by the direct detection of pregnane and/or tetrahydrocortisone, which is discussed in more detail in Example 2 below. It will be appreciated, that the techniques described in Example 2 can be used to detect tetrahydrocortisone. Alternatively, when the composite superhydrophobic material is used in combination with metal nanoparticles, the SERS detection may be by indirect means, whereby quantification of the analytes is obtained by their influence on the SERS spectra of the boronic acid (see Examples 3-6 below). It is noted that the silver and/or gold nanoparticles coated with boronic acid comprising a thiol group may provide a "mirror effect" that further enhances the analytical enhancement factor of the substrate, as described in more detail in the examples below.

The silver and/or gold nanoparticles of the urine analysis formulation may be formed from the same metals as those used to form that composite superhydrophobic material. That is, if the superhydrophobic material is formed using silver for the metal nanoparticles and the metal layer, then the nanoparticles of the urine analysis formulation may be silver nanoparticles. If the superhydrophobic material is formed using gold for the metal nanoparticles and the metal layer, then the nanoparticles of the urine analysis formulation may be gold nanoparticles and so on.

Any suitable boronic acid may be used, and examples of suitable boronic acids are provided by compounds of formula I below:

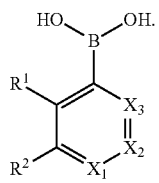

I where:
$X_1$ is N or $CR^3$;
$X_2$ is N or $CR^4$;
$X_3$ is N or $CR^5$;
$R^1$ to $R^5$ independently represent H, $B(OH)_2$, $CH_3$, CHO, $CO_2H$, CN, $NH_2$, OH, SH, $NO_2$, F, Br, Cl,
wherein none or one of $X_1$ to $X_3$ is N, and provided that when one of $X_1$ to $X_3$ is N, then $R^1$ to $R^5$ independently represent H, $B(OH)_2$, CHa, $CO_2H$, CN, $NH_2$, OH, SH, $NO_2$, F, Br, Cl.

A suitable boronic acid that may be mentioned herein is 4-mercaptophenylboronic acid.

The nanoparticles of the urine analysis formulation may have any suitable size or shape. For example, the nanoparticles of the urine analysis formulation may be in the form of a spheroid or a polyhedron, such as a cube. Said nanoparticles may have any suitable surface area, such as from 50,000 to 150,000 $nm^2$. In a particular example that may be mentioned herein, the nanoparticles of the urine analysis formulation may be in the form of a cube having an edge length of 128.9 nm, which provides a surface area of 99,810.4 $nm^2$. If the boronic acid is 4-mercaptophenyl boronic acid, then this molecule is estimated to have a surface area of around 0.34 $nm^2$ when bound to the surface of the nanoparticle. Thus, the total number of 4-mercaptophenylboronic acid molecules bound to the surface of the cube's surface (assuming complete coverage) is estimated to be 293,560 molecules.

As outlined in PCT patent application publication No. WO 2018/199849, which is incorporated herein in its entirety by reference, the levels of certain molecules in the urine of a pregnant female may be used to ascertain the risk of miscarriage in a subject. While any or all of the molecules indicated in WO 2018/199849 may be used in combination with the kit of parts described above using SERS, it has been found that pregnane (i.e. 3α,20α-dihydroxy-5-pregnane-3-glucuronide or 5β-pregnane-3α,20α-diol glucuronide) and tetrahydrocortisone may be particularly useful in such a method. Thus, there is provided a method of predicting increased risk of spontaneous miscarriage, the method comprising the steps of:
(a) providing an aqueous solution comprising the non-salt components of a urine sample obtained from a subject;
(b) reacting the aqueous solution with a urine analysis formulation comprising silver and/or gold nanoparticles coated with a boronic acid comprising a thiol group for a first period of time to provide a complexed sample, optionally wherein the nanoparticles are formed from the same metal(s) used in the composite superhydrophobic material and/or the boronic acid is 4-mercaptophenylboronic acid;
(c) placing the complexed sample onto a composite superhydrophobic material as described above and removing the water by evaporation to provide a dried sample; and
(d) subjecting the dried sample to Raman spectroscopy to determine the abundance of pregnane and tetrahydrocortisone and then predicting the risk of spontaneous miscarriage based on the formula:

$$\frac{\text{Pregnane Abundance}}{(\text{Pregnane Abundance} + \text{Tetrahydrocortisone Abundance})} \times 100\%$$

wherein a value lower than a threshold value is indicative of increased risk of spontaneous miscarriage, optionally wherein the first period of time is from 3 to 48 hours, such as 3 hours.

As described herein (and in WO 2018/199849), a ratio of pregnane/tetrahydrocortisone of 76 indicates a stable pregnancy and its corresponding pregnane percentage is 98.7%. A ratio of pregnane/tetrahydrocortisone of 38 indicates a miscarriage risk and the corresponding pregnane percentage is 97.4%.

While reaction step (b) above may be conducted at any suitable pH, the reaction may proceed most smoothly at in a pH range of from 10 to 12, such as 11. In some embodiments where the pH of step (b) is from 10 to 12, the product of step (b) may be centrifuged for a second period of time and the supernatant removed and replaced with a liquid, such as aqueous KOH, having a pH of from 10 to 12, such as 11 and this centrifugation, supernatant removal and liquid replacement steps may be repeated a further one to four times, such as a further two times before step (c) of the above method is conducted.

The aqueous solution used in step (a) of the above-mentioned process may be obtained by the following steps:
(i) adding a urine sample comprising salt and non-salt components obtained from a subject onto a reverse phase column to provide a loaded column;
(ii) removing the salt components from the loaded column by eluting with water, then removing and isolating the non-salt components from the loaded column by eluting with a $C_{1-4}$ alcohol (e.g. methanol) and then removing the $C_{1-4}$ alcohol; and
(iii) adding an aqueous solution to the isolated non-salt components to provide the aqueous solution of step (a). In certain embodiments, the aqueous solution of step (a) may have a pH of from 10 to 12, such as 11.

While any suitable setting for Raman spectroscopy may be chosen, a convenient set of conditions that may be mentioned herein is where the Raman spectroscopy is conducted using a laser excitation wavelength of 532 nm, using a laser power of from 0.01 to 1 mW and an acquisition time of from 1 to 60 seconds. For example, the laser power may be 0.2 mW and the acquisition time may be 1 second.

The number of spectra taken for each sample may be from 10 to 5,000 SERS spectra, such as from 20 to 2,000 SERS spectra. In embodiments of the invention, a total of 30 SERS spectra may be optimal.

As will be appreciated, before the real samples are run, background scans of the superhydrophobic (SPHB) substrate itself are conducted to ensure that there are no interfering signals arising from 11-mercaptoundecanoic acid. The sample is only run when the base line for the SERS signal from SPHB substrate background is flat and featureless. To establish the calibration curve, SERS experiments and analyses were run using urine samples of non-pregnant women spiked with different amounts of 90-100% pregnane/tetrahydrocortisone concentration ratios. This calibration curve was then used to predict the relative abundance of pregnane compared to THC in the tested samples. It is noted that analyte-specific calibration curves are required for quantification of each specific analyte.

Further details of the SERS analysis is provided in the examples section below.

Further aspects and embodiments of the invention will now be discussed with respect to the following non-limiting examples.

EXAMPLES

Materials

Silver nitrate (≥99%), anhydrous 1,5-pentanediol (PD, ≥97%), poly(vinylpyrrolidone) (PVP, average MW=55,000 g/mol), toluene (99.5%), 11-mercaptoundecanoic acid (95%), 4-mercaptophenylboronic acid (90%), ammonia solution (28-30%), 1H,1H,2H,2H-perfluorodecanethiol (PFDT, 97+%) were purchased from Sigma Aldrich. Copper (II) chloride (≥98%), 3-aminopropyltriethoxysilane (98%) were purchased from Alfa Aesar. Ethanol (ACS, ISO, Reag. Ph Eur) was purchased from EMSURE; hydrochloric acid (HCl, 37%) was purchased from Analar Normapur. Tetrahydrocortisone (THC) was purchased from Scientific Resources. 5β-pregnane-3α,20α-diol glucuronide (referred to as "pregnane") was purchased from AXIL Scientific Pte Ltd. All chemicals were used without further purification. Milli-Q water (>18.0 MΩ·cm) was obtained using a Sartorius Arium 611 UV ultrapure water system.

General Methods

SEM imaging was performed using a JEOL-JSM-7600F microscope at an accelerating voltage of 5 kV. UV-vis spectroscopic measurements were performed with a Cary 60 UV-Vis spectrometer. Zeta potential measurements were conducted using ZETASIZER NANO with DTS1070 folded capillary cell. Thermal evaporation of Ag was performed using Syskey Thermal Evaporator (Taiwan). Roughness of the sample was measured using JPK Nanowizard 3 BioScience atomic force microscopy (AFM) on a Zeiss inverted microscope. x-y SERS measurements were performed with Ramantouch microspectrometer (Nanophoton Inc, Osaka, Japan) at an excitation wavelength of 532 nm (power of 0.01-1 mW, and acquisition time of 1-60 s). A 20× (N.A. 0.45) objective lens with 10 s accumulation time was used for data collection between 500 $cm^{-1}$ to 1600 $cm^{-1}$. All SERS spectra were obtained by averaging at least 10 individual spectra per Raman image. ZIPTIPs (Merck Millipore) packed with a C18 column were used for sample pretreatment. PCA and PLS analysis were carried out using the Panorama software (LabCognition, Analytical Software GmbH & Co. KG).

Contact Angle Measurements

Contact angles were measured using a Theta Lite tensiometer equipped with a Firewire digital camera. Static contact angles were measured by dropping a sessile droplet of 4 µL of water droplet onto the substrate. The angle formed between the solid-liquid interface and liquid-air interface is the static contact angle. Advancing contact angle was measured as the maximal contact angle measured by slowly adding small amount of liquid (20 µL) to the droplet. During the addition of liquid, the contact line remained while the contact angle increased during wetting process. Receding contact angle was also measured as the minimum contact angle when a small amount of liquid was removed slowly from the droplet. During the removal of liquid, the contact line remained while the contact angle decreased during de-wetting process. The difference between the advancing contact angle and receding contact angle gave rise to the contact angle hysteresis. Each type of contact angle measurement was performed at least five times across each substrate to obtain an average wetting angle.

Liquid Concentrating Effect of the Substrates

To determine the liquid concentrating effect of the substrates, silica particle suspension synthesised using a modified Stöber process was used on the substrates.

Typically, a mixture of deionised water (1.5 mL) and ammonia solution (1.5 mL) was added dropwise into a tetraethyl orthosilicate ethanolic solution (0.35 M, 0.76 mL) under vigorous stirring for 30 min. The silica beads were obtained by centrifugation, washed with ethanol and water, and subsequently redispersed in deionised water. 1 µL of the water-soluble silica beads were drop-cast onto the respective superhydrophobic substrate and the $O_2$ plasma treated Si substrate (hydrophilic substrate), respectively, and left to dry under ambient conditions. The dried spots were then characterised by SEM and the surface areas on both superhydrophobic and hydrophilic surfaces were measured using ImageJ software.

General Procedure 1—Synthesis and Purification of Silver Nanocubes (AgNC)

The preparation of silver nanocubes (AgNC) was carried out according to the polyol method described in Angew. Chem. Int. Ed. 2006, 45, 4597. Typically, two 10 mL solutions of $CuCl_2$ (8 mg/mL) and PVP (20 mg/mL) were first prepared separately by vortexing and sonicating the mixture repeatedly till the solids dissolved fully in PD. 35 µL of the $CuCl_2$ solution was then added to a solution of $AgNO_3$ (20 mg/mL, 10 mL), vortexed and sonicated repeatedly till the solids dissolved completely.

To a 100 mL round bottom flask which has been cleaned with aqua regia and heated at 190° C. for 10 min, 20 mL of 1,5-pentanediol (PD) was added, followed by the dropwise addition of 250 µL of poly(vinylpyrrolidone) (PVP) solution (PVP stabilises AgNC) to the mixture at every 30 s, and the addition of 500 µL of the $AgNO_3$ solution (containing $CuCl_2$) quickly at every minute. This process was continued until the reaction mixture turned reddish brown. For the subsequent growth of silver nanooctahedra (AgNO) in "General Procedure 2", this solution was used without further treatment.

To purify the AgNC for further self-assembly experiments, acetone was added to the AgNC solution and centrifuged to remove excess PD. The supernatant was then dispersed in ethanol to remove excess acetone. The resulting suspension was dispersed in 10 mL of ethanol and subsequently diluted with 100 mL of aqueous PVP solution (0.2 g/L). The mixture was then vacuum filtered using PVDF filter membranes with pore sizes 5000, 650, 450 and 220 nm for several times on each pore size.

Figure 1:
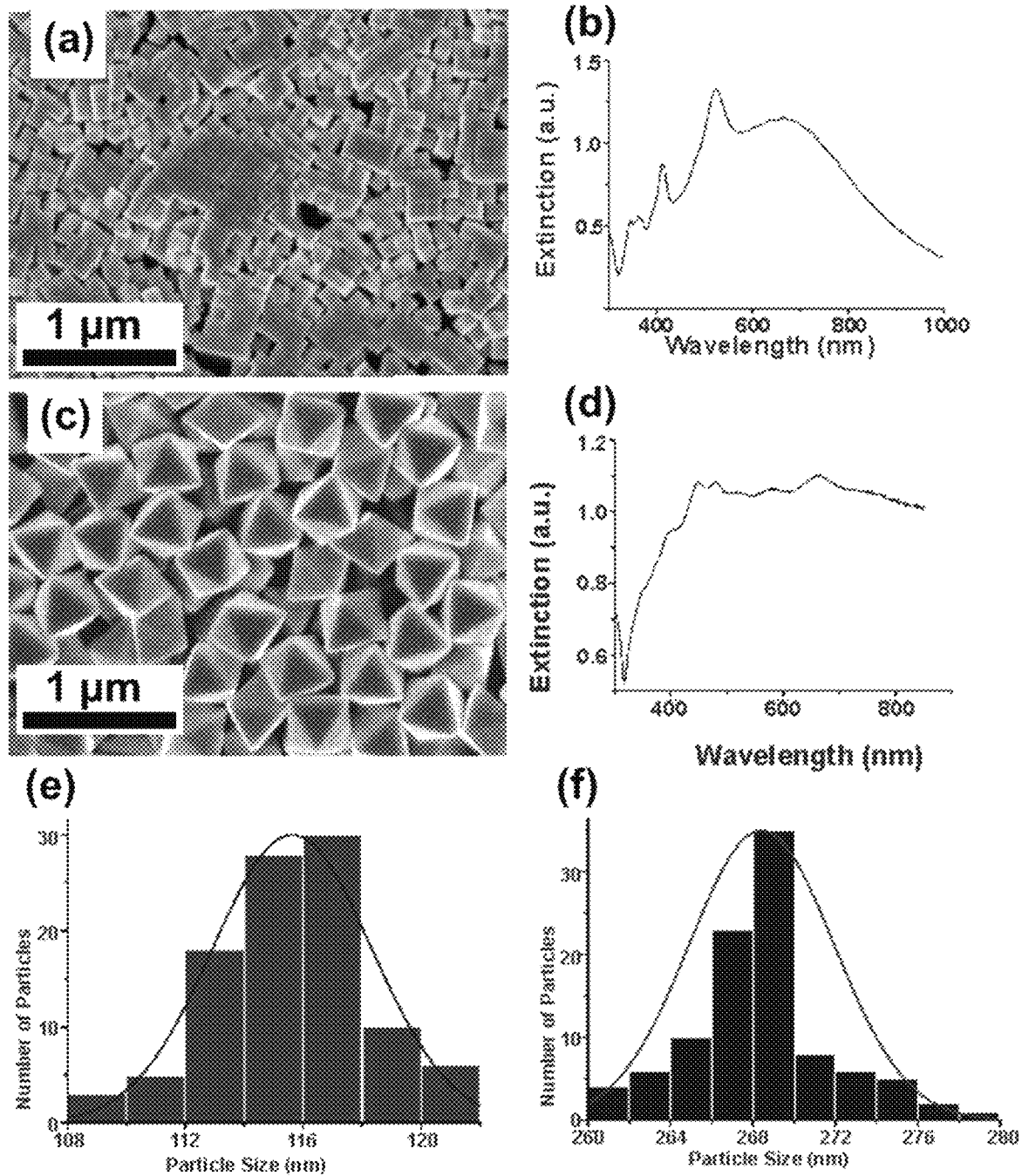
FIG. 1 Depicts: (a, c) the SEM images; (b, d) absorption spectra; and (e, f) the size distribution of AgNC and AgNO used in embodiments of the current invention.
Figure 2:
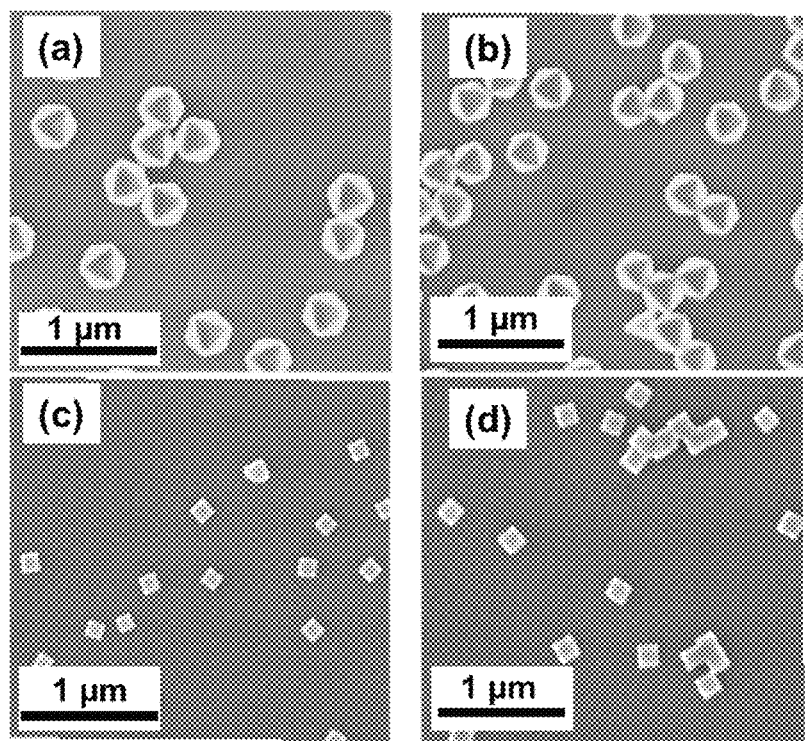
FIG. 2 Depicts the SEM images of: (a, b) AgNO; and (c, d) AgNC in water and ethanol respectively.

The initial batch of AgNC was characterised by UV-vis spectroscopy and SEM imaging to determine the absorbance (plasmon resonances) and the edge length of AgNC (FIGS. 1a and 1b). The edge length was measured in the SEM images using ImageJ software and was determined to be 116±3 nm (FIG. 1e).

For a subsequent, optimised batch of AgNC, the edge lengths were measured and analysed using ImageJ software for 100 particles, and was determined to be 128±7 nm. The as-synthesised AgNC had an approximate concentration of 2 mg/mL, with a particle concentration of $1.2 \times 10$ particles/mL.

General Procedure 2—Synthesis and Purification of Silver Nanooctahedra (AgNO)

The synthesis of AgNO was carried out using the AgNC synthesised in "General Procedure 1". Precursor solutions of $CuCl_2$ (8 mg/mL) and PVP (20 mg/mL) were first prepared separately by vortexing and sonicating the mixture repeatedly in 10 mL of PD, till the solids dissolved fully. 40 µL of the $CuCl_2$ solution was then added to a $AgNO_3$ solution (40 mg/mL in PD), vortexed and sonicated repeatedly till fully dissolved.

The round bottom flask containing the as-synthesised AgNC solution in PD was heated to 190° C. for 10 min. This was then followed by the addition of 250 µL of PVP solution dropwise to the mixture at every 30 s, and the addition of 500 µL of the $AgNO_3$ solution (containing $CuCl_2$) quickly at every minute. This process was continued for approximately an hour, and the reaction mixture became greyish brown.

To purify the as-synthesised AgNO, acetone was added to the AgNO solution and centrifuged at 8000 rpm for 10 min to remove excess PD, followed by dispersing in 10 mL of ethanol to remove excess acetone. The resulting suspension was then re-dispersed in 10 mL of ethanol (AR grade) and then diluted with 100 mL of aqueous PVP solution (0.2 g/L). The mixture was then vacuumed filtered using PVDF filter membranes with pore sizes 5000 and 650 nm for several times on each pore size.

The initial batch of AgNO was characterised by UV-vis spectroscopy and SEM imaging to determine the absorbance (plasmon resonances) and the edge length of AgNO (FIGS. 1c and d). The edge length was measured in the SEM images using ImageJ software and was determined to be 270±6 nm (FIG. 1f).

For the subsequent, optimised batch of AgNO, the edge lengths were measured and analysed using ImageJ software for 100 particles, and was determined to be 299±22 nm. The as-synthesised AgNO had an approximate concentration of 13.7 mg/mL, with a particle concentration of $1.2 \times 10^{11}$ particles/mL.

General Procedure 3—Preparation of Negatively-Charged AgNC (85) and AgNO (90)

Typically, 1 mL of ethanol was added to the AgNC solution (0.1 mL, 1.2×10 particles/mL), followed by centrifugation with the supernatant discarded. The AgNC was then re-dispersed in 1.5 mL of IPA/ethanol (1:1, v/v) and left stirring at 500 rpm at 25° C. A solution of 11-mercaptoundecanoic acid (11-MUA, 0.05 mL, 0.1 mM) in IPA was then added dropwise to the stirring solution of AgNC and the reaction mixture was left to stir at room temperature for 4 hr. The reaction mixture was then removed from stirring and centrifuged at 6500 rpm for 4.5 min to remove the supernatant. The process was repeated once more, and the AgNC was incubated with a fresh solution of 11-MUA in IPA for a further 3 hr. Thereafter, the resulting solution was centrifuged with the supernatant removed. The AgNC was then dispersed in 1.5 mL of IPA/ethanol (1:1, v/v), sonicated and centrifuged. The process was repeated twice and the resulting negatively-charged AgNC (80) was stored in a nitrogen environment to prevent oxidation. Zeta potential measurement was also carried out to ensure that the AgNC was negatively charged.

The above synthesis process was repeated for four separate AgNO solutions (0.1 mL, $1.2 \times 10^{11}$ particles/mL), using a solution of 11-MUA (0.1 mL, 10 mM) in IPA, to give the negatively-charged AgNO (90). The zeta potential of AgNO was determined to be about −27 mV.

The zeta potential for the initial batch of AgNC and AgNO, functionalised with 11-MUA, were measured with the samples dispersed in water and ethanol respectively (Table 1). In addition, the SEM images of AgNC and AgNO in water and ethanol are as shown in FIGS. 2a-d.

TABLE 1

| Zeta potential measurements of the initial batch of AgNC and AgNO in water and ethanol respectively | | | |
|---|---|---|---|
| Sample | Functionality | Solvent | Zeta potential (mV) |
| AgNC | 11-mercaptoundecanoic acid | Water | −23.5 |
| | | Ethanol | −2.12 |
| AgNO | | Water | −22.7 |
| | | Ethanol | 0.99 |

General procedure 4—Functionalisation of AgNC with 4-mercaptophenylboronic acid (4-MPBA)

The functionalisation of AgNC with 4-MPBA was identical to the procedure as described in "General Procedure 3", except that the solution of 11-MUA (0.05 mL, 0.1 mM) in IPA was replaced with a solution of 4-MPBA (0.05 mL, 0.1 mM) in IPA.

Typically, 1 mL of ethanol was added to the AgNC solution (0.1 mL, 1.2×10$^{11}$ particles/mL), followed by centrifugation with the supernatant discarded. The AgNC was then re-dispersed in 1.5 mL of IPA/ethanol (1:1, v/v) and left stirring at 500 rpm at 25° C. A solution of 4-MPBA (0.05 mL, 0.1 mM) in IPA was added dropwise to the stirring solution of AgNC and the reaction mixture was left to stir at room temperature for 4 hr. The reaction mixture was then removed from stirring and centrifuged at 6500 rpm for 4.5 min to remove the supernatant. The process was repeated once more, and the AgNC was incubated with a fresh solution of 4-MPBA in IPA for a further 3 hr. Thereafter, the resulting solution was centrifuged with the supernatant removed. The AgNC was then dispersed in 1.5 mL of IPA/ethanol (1:1, v/v), sonicated and centrifuged. The process was repeated twice and the resulting functionalised AgNC was stored in a nitrogen environment to prevent oxidation. The as-synthesised boronic acid functionalised AgNC is denoted as "AgNC/4-MBPA" in the subsequent examples.

The boronic acid functionality on the AgNC allows the capture of urine metabolites (e.g. THC and pregnane) to the surface of the AgNC. This is done by having the hydroxyl groups on THC and pregnane to undergo condensation reactions with the boronic acids under alkaline conditions to form boronate esters in the solution (FIGS. 14a, c and d).

The density of the 4-MPBA on the AgNC surface was estimated as shown in the calculations below.

Figure 3:
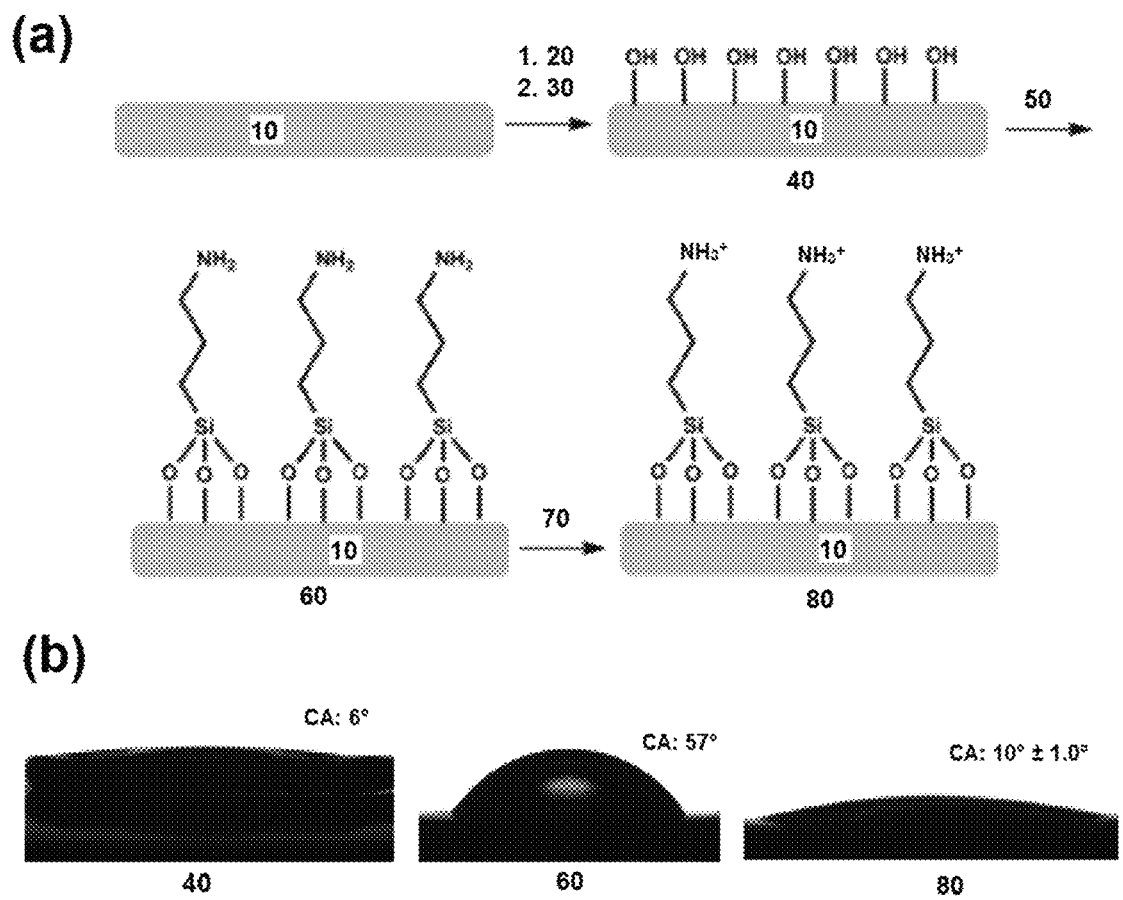
FIG. 3 Depicts: (a) a schematic representation of the surface functionalisation of silicon substrates; and (b) the static contact angles of treated or functionalised substrates 40, 60 and 80.

Edge length of the AgNC=128.9 nm
Surface area of AgNC=6×(128.9 nm)$^2$=99,810.4 nm$^2$
Estimated surface area of a 4-MPBA molecule (derived from simulations)=0.34 nm$^2$
No. of 4-MPBA molecules on AgNC surface (assumed full coverage)=99810.4/0.34=293,560 molecules General Procedure 5—Surface Functionalisation of Silicon Substrates Typically, a silicon (Si) substrate 10 was cleaned with a mixture of $H_2SO_4/H_2O_2$ 20 or subject to oxygen plasma treatment 30 for 5 min (FIG. 3a). The treated substrate 40 was then submerged in an anhydrous toluene solution with 3-aminopropyltriethoxysilane (2% by volume) 50 for 5 min to functionalise the Si substrates. Subsequently, the amine-terminated Si substrate 60 was rinsed with anhydrous toluene and methanol, followed by blow drying with $N_2$ gas to remove any ligands and solvents. The functionalised substrate was then submerged in a hydrochloric acid solution of pH 5 (70) for an additional 5 min to further protonate the substrate surface and render it positively-charged. The resulting substrate 80 was then kept in a nitrogen environment for further use. The static contact angles of the various treated substrates 40, 60 and 80 were determined and as shown in FIG. 3b.

General Procedure 6—Synthesis of Silver Nanosphere (AgNS)

The synthesis of AgNS was carried according to the method described in *Chem. Mater.* 2014, 26, 2836-2846. Typically, a 100 mL of aqueous solution containing 5 mM of sodium citrate and 0.1 mM tannic acid was prepared and heated in a three-neck round-bottomed flask for 15 min under vigorous stirring. 1 mL of $AgNO_3$ (25 mM) was then added into this boiling solution. The solution became bright yellow immediately. The resultant AgNS was purified by centrifugation (10,000 g to 18,000 g, depending on its size) in order to remove the excess of TA and re-dispersed in Milli-Q-water or sodium citrate solution (2.2 mM) before sample characterisation. The zeta potential of the AgNS was determined to be −30 mV and the size of the AgNS was approximately 41 nm (FIGS. 19a and b).

Example 1. Fabrication and Characterisation of Superhydrophobic Substrate

Initial Batch of Superhydrophobic Substrate 107
Fabrication of the Initial Batch of Superhydrophobic Substrate 107

Figure 4:
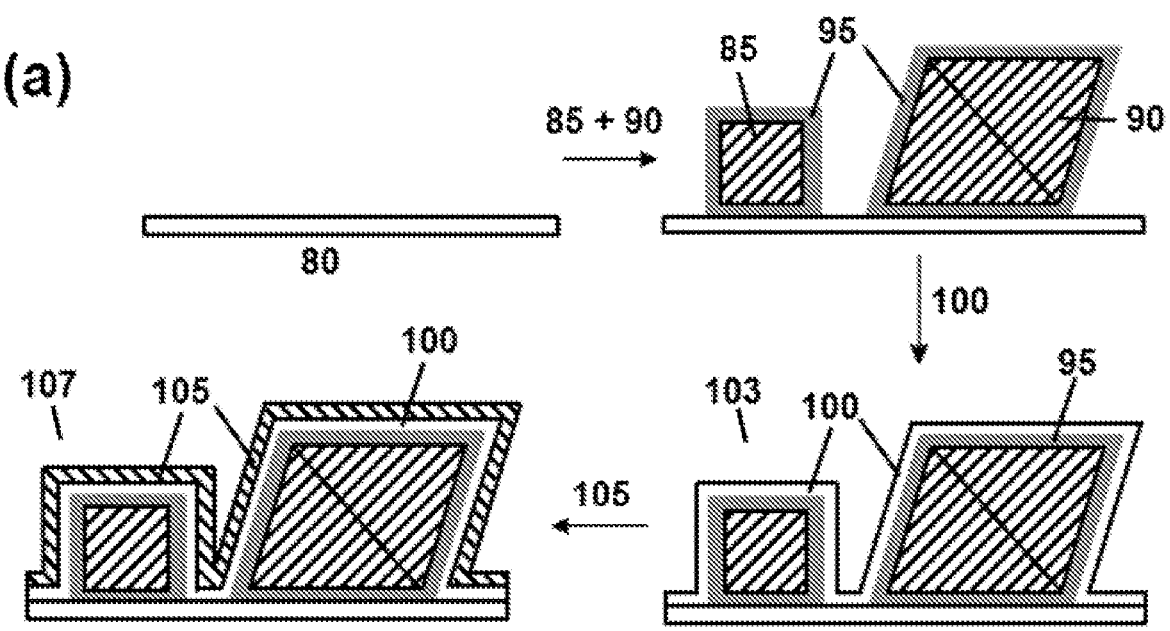
FIG. 4 Depicts a schematic representation of the fabrication of: (a) the initial batch of superhydrophobic substrate 107; and (b) the optimised batch of superhydrophobic substrate 109.
Figure 4:
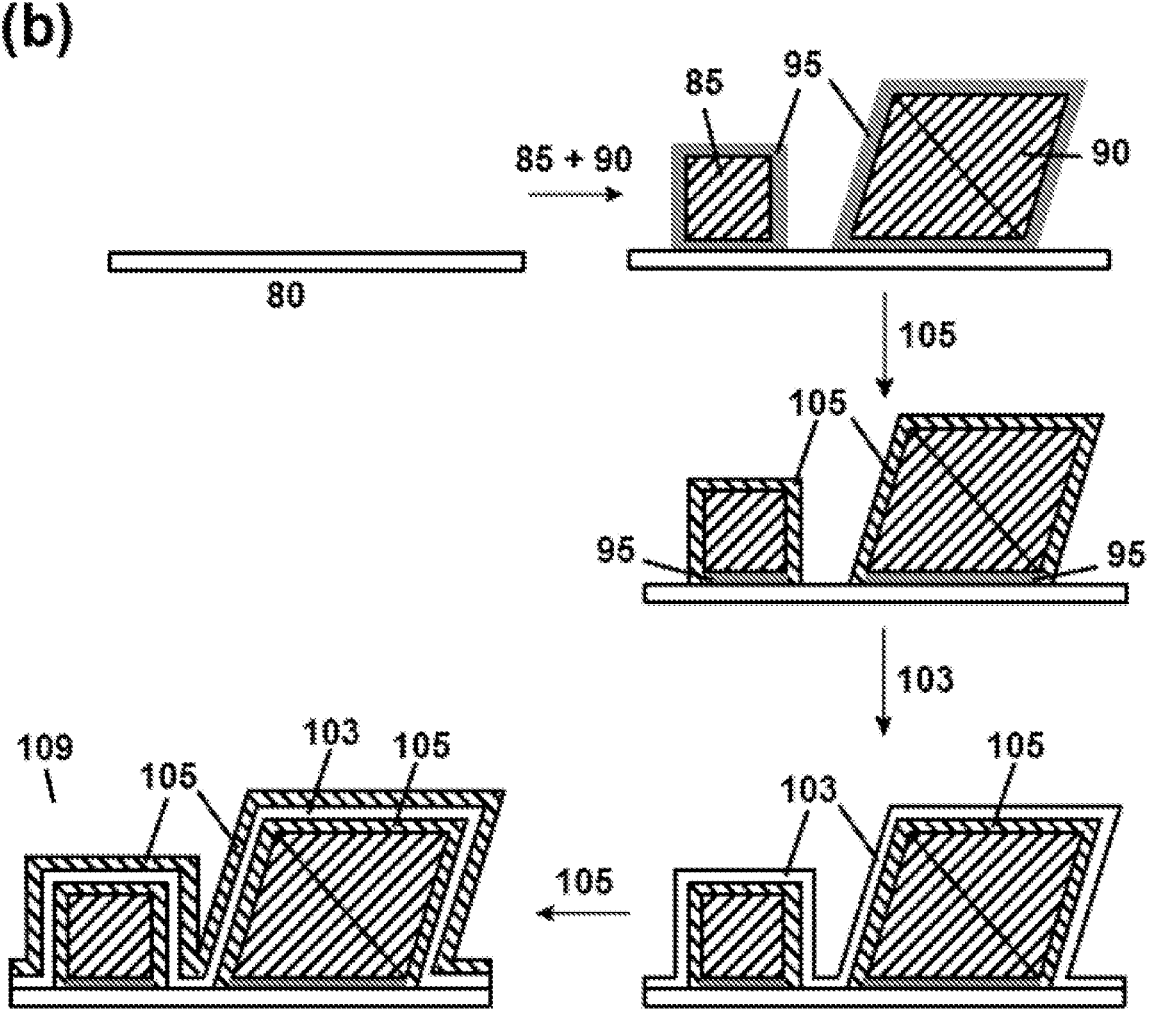

Electrostatic self-assembly was performed by submerging the positively-charged Si substrate 80 (as-prepared from "General Procedure 5") into 2 mL of negatively charged aqueous Ag nanoparticle mixture which comprised of AgNO (85) and AgNC (90) in a particle ratio of 5:1 for 100 min (FIG. 4a). Self-assembly occurred via electrostatic attraction, with the COO-functionality of the 11-MUA layer 95 on the Ag nanoparticles binding to the $NH_3^+$ terminal of substrate 80. This self-assembly approach generated a monolayer of Ag nanoparticles. The binary self-assembled substrate was removed from the aqueous Ag nanoparticle mixture, rinsed with ethanol and blown dry using $N_2$ gas twice.

The resulting substrate was then coated with a metal layer (100) of 2 nm of Cr, followed by 25 nm Ag, at 0.1 and 0.5 Å/s, respectively, via thermal evaporation. This helps to improve adhesion of the binary Ag nanoparticles to the substrate 80. The substrate was then submerged in a solution of 1H,1H,2H,2H-perfluorodecanethiol (PFDT) 105 (5 mM in 1:1 ethanol/hexane, v/v) overnight to give the superhydrophobic substrate 107.

Figure 6:
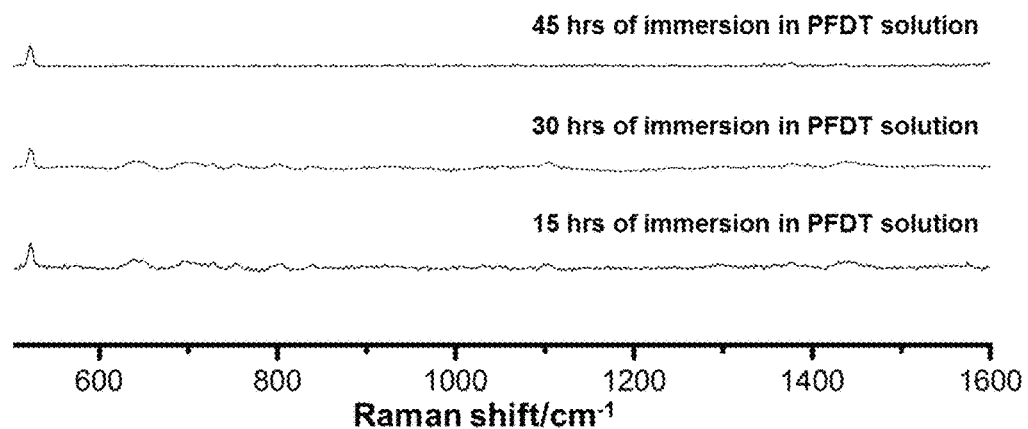
FIG. 6 Depicts the SERS spectra of the superhydrophobic substrate 107 after 15 to 45 hr of immersion in PFDT solution.

To create a clean spectral background in subsequent SERS measurements, the substrate was immersed in 5 mM of PFDT solution for 15 hr, washed with ethanol and blown dry for at least six times to remove excess PFDT solution. The solution was replaced with fresh PFDT solution after every cycle of immersion. It was observed that the SERS background noise of the substrate was reduced with longer submerging time of 45 hr (FIG. 6).

Effect of Functionalising the Substrate with PFDT on its Hydrophobicity

The static contact angles of substrates 103 and 107 were measured to determine the effect of coating the substrate with PFDT on their hydrophobicity. The static contact angles for both substrates were determined after 20 min and 40 min of incubation with Ag nanoparticles, and are as shown in Table 2.

TABLE 2

Static contact angles of substrates functionalised and not functionalised with PFDT

| Functionalisation | Contact angle after 20 min of incubation with the Ag nanoparticles | Contact angle after 40 min of incubation with Ag nanoparticles |
|---|---|---|
| Functionalised with PFDT (Substrate 107) | 156° ± 1.8° | 156° ± 0.9° |
| Not functionalised with PFDT (Substrate 103) | 102° ± 1.7° | 137° ± 2.7° |

Effect of Incubation Time of the Substrate 80 in the Ag Nanoparticle Mixture (85+90) on the Hydrophobicity of Substrate 107

To investigate the effect of incubation time of substrate 80 in the Ag nanoparticle suspension on the hydrophobicity of the substrate, the procedure described above was repeated with different incubation time of 20 to 120 min to give the respective substrates 107.

Figure 5:
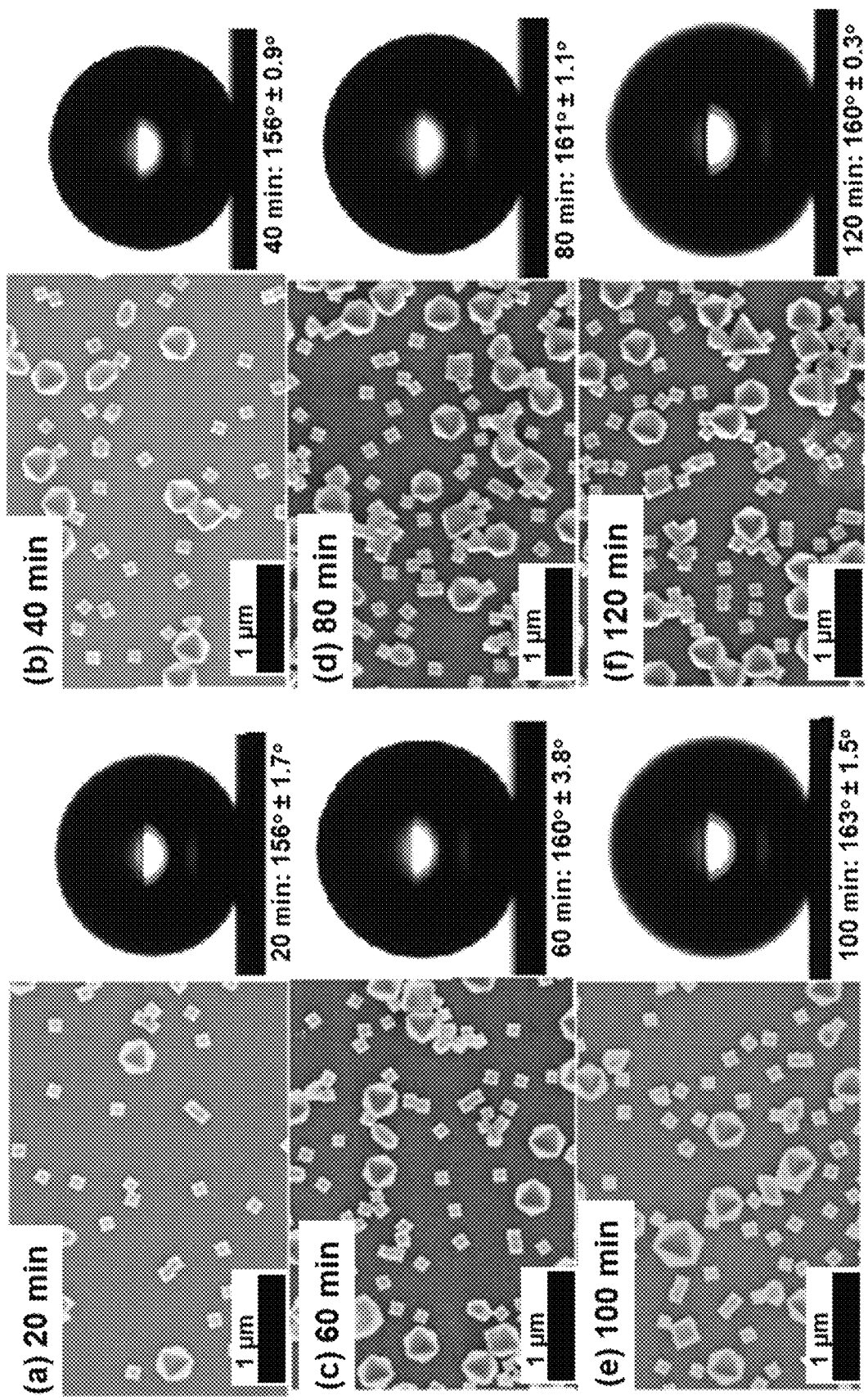
FIG. 5 Depicts the SEM images and static contact angle of the superhydrophobic substrate 107 prepared using an incubation time of the substrate 80 in the Ag nanoparticles mixture from (a-f) 20 to 120 min.

The SEM images and the static contact angles of the various substrates 107 treated with the Ag nanoparticles with different incubation times were determined and as shown in FIG. 5. It was observed that incubating the substrate 80 with the Ag nanoparticles for 100 min gave the highest contact angle of 163°±1.5°.

The particle density and contact angle hysteresis were also determined and are as shown in Table 3. It was observed that a longer incubation time gave a higher particle density and a lower contact angle hysteresis.

TABLE 3

Particle density and contact angle hysteresis of substrates with various incubation time with the Ag nanoparticles

| Time (min) | Particle density (no. of particles/μm$^2$) | Contact angle hysteresis |
|---|---|---|
| 20 | 3.74 ± 0.01 | 32.35° ± 1.07° |
| 40 | 5.3 ± 0.66 | 29.26° ± 0.37° |
| 60 | 7.59 ± 0.27 | 27.36° ± 0.79° |
| 80 | 8.37 ± 0.20 | 19.23° ± 1.45° |
| 100 | 9.19 ± 0.12 | 16.57° ± 1.62° |
| 120 | 10.13 ± 0.58 | 14.23° ± 0.42° |

Effect of Having a Binary Assembly of AgNC and AgNO on the Hydrophobicity of Substrate 107, as Compared to Having AgNC or AgNO Alone To understand the effect of having a binary assembly of AgNC and AgNO on the hydrophobicity of the substrate, substrates containing only AgNC or AgNO were synthesised according to the procedure above, with an incubation time of 100 min.

Figure 7:
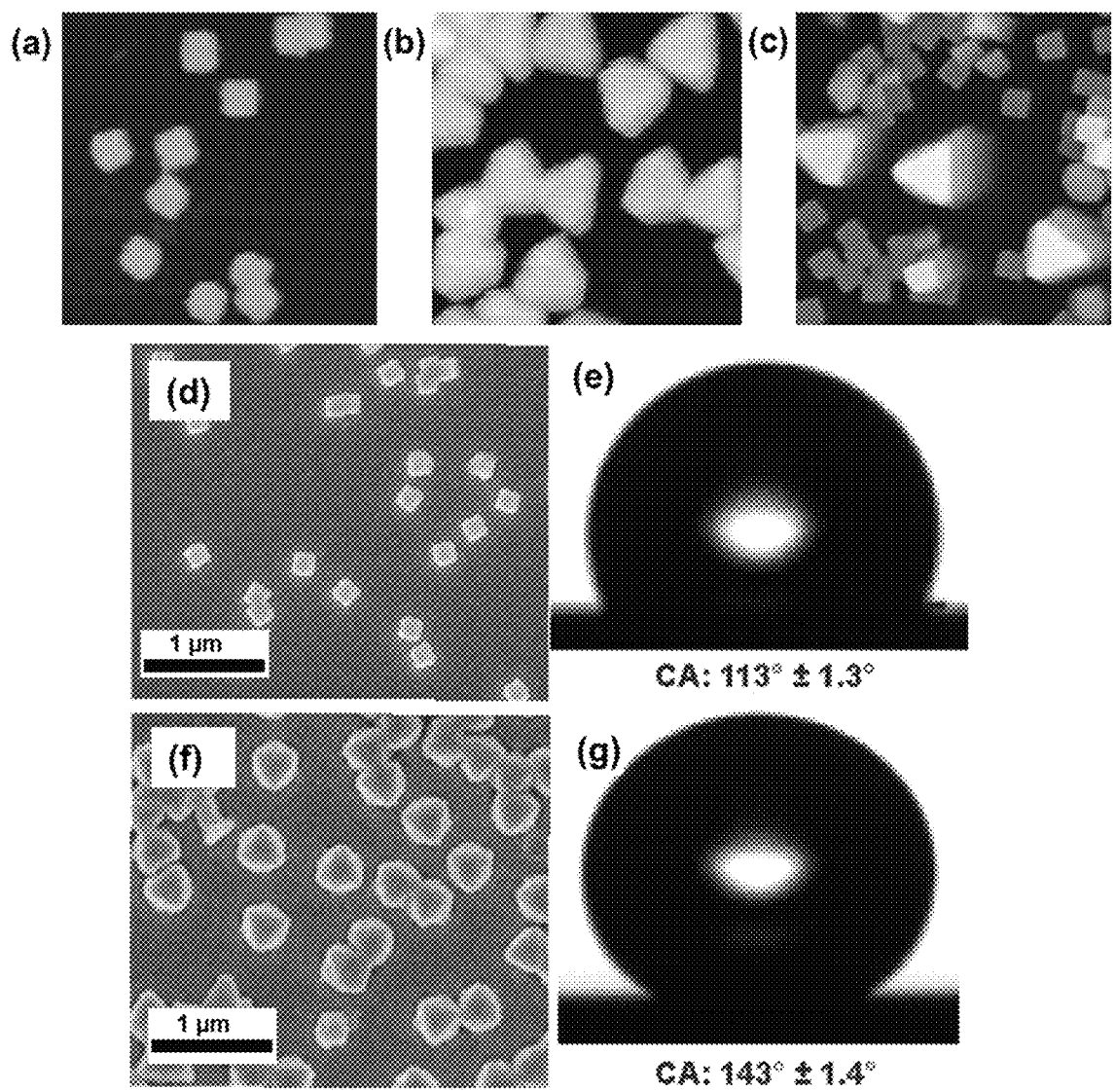
FIG. 7 Depicts: (a-c) the AFM images of the substrates containing AgNC, AgNO, and both AgNC and AgNO, respectively; (d, e) the SEM image and static contact angles of the substrate containing AgNC only; (f, g) the SEM image and static contact angles of the substrate containing AgNO only.

The static contact angles and the root mean square (RMS) surface roughness of the substrates were determined and as shown in Table 4. The AFM images of the respective substrates are as shown in FIGS. 7a-c, and the SEM images and static contact angles of the AgNC and AgNO substrates are shown in FIGS. 7d and e, and FIGS. 7f and g respectively.

TABLE 4

Static contact angles and RMS surface roughness of substrates having both AgNC and AgNO, in comparison to substrates having AgNC or AgNO alone.

| Sample | Static contact angle | RMS surface roughness |
|---|---|---|
| AgNC and AgNO | 163° ± 1.5° | 90 nm ± 6 nm |
| AgNC only | 113° ± 1.3° | 47 nm ± 8 nm |
| AgNO only | 143° ± 1.4° | 103 nm ± 10 nm |

Liquid Concentrating Effect of Substrate 107 in Comparison to a Hydophilic Substrate The liquid concentrating effect of substrate 107 was determined according to the procedure described above in "liquid concentrating effect of the substrates".

Figure 8:
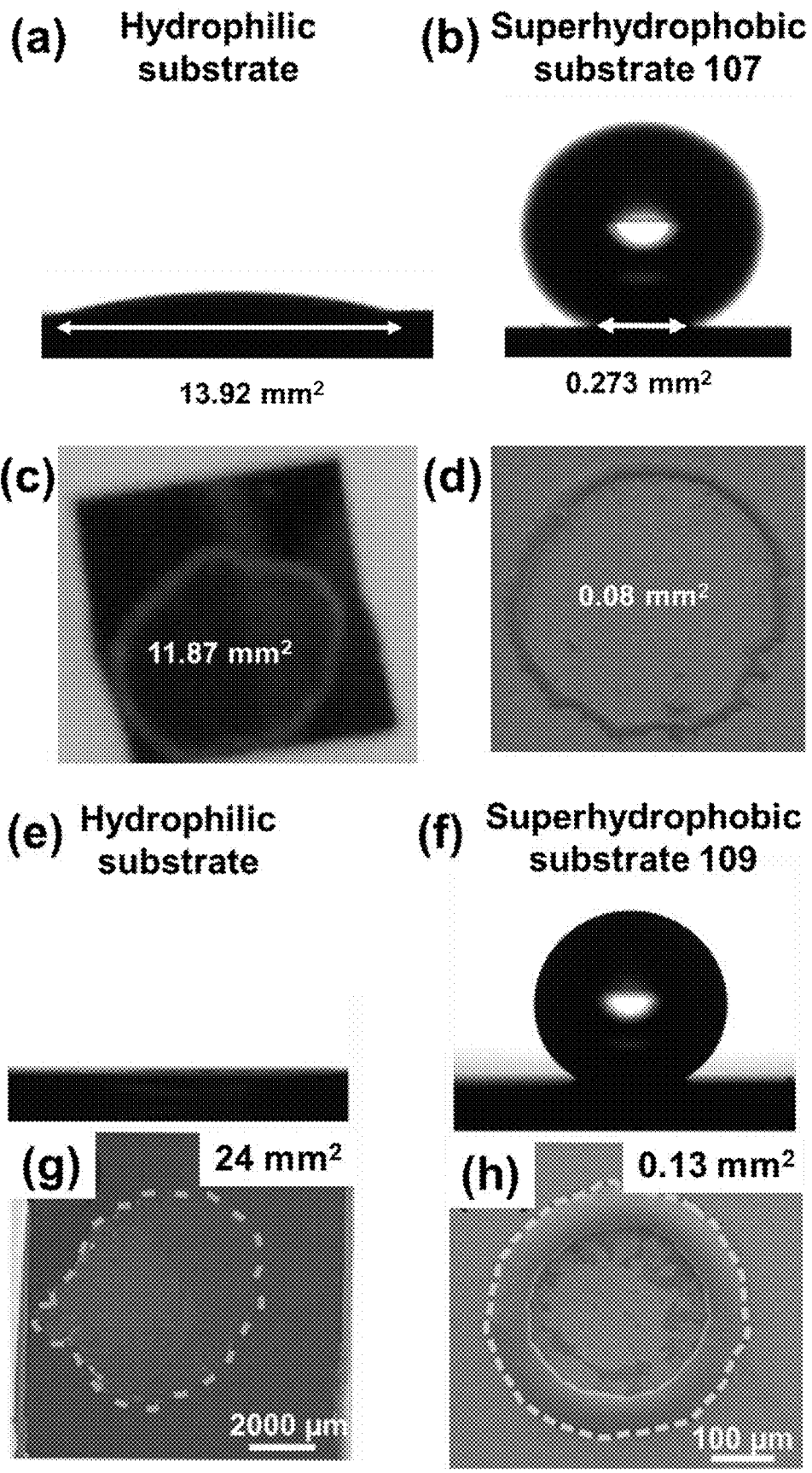
FIG. 8 Depicts the liquid concentrating effect of the superhydrophobic substrate in comparison to a hydrophilic substrate: (a, b) static contact angle of the hydrophilic and superhydrophobic substrate 107, respectively; (c) optical image of a spot area of a dried sample on the hydrophilic substrate; (d) SEM image of a dried sample on substrate 107.

Comparing the droplet of silica suspension on substrate 107 and the hydrophilic substrate, it was observed that there was a 51-fold reduction of the liquid-solid contact area on substrate 107 (FIGS. 8a and b). Upon drying of the droplet on substrate 107, the dried contact area was measured to be 0.08 mm$^2$, which was a further 3.4-fold reduction from the contact area prior to drying (FIGS. 8b and d). On the other hand, there was only a 1.2-fold reduction of contact area for the hydrophilic substrate upon drying. Therefore, the overall concentrating effect of the superhydrophobic substrate was determined to be approximately 148-fold.

As such, the significant reduction of the contact area of the analyte sample on the superhydrophobic substrate 107 can lead to a concentrating of the analytes into a smaller area which is required for sensitive detection.

Optimised and Improved Batch of Superhydrophobic Substrate 109

Fabrication of the Optimised Batch of Superhydrophobic Substrate 109

Electrostatic self-assembly was performed by submerging the positively-charged Si substrate 80 (as-prepared from "General Procedure 5") into 2 mL of negatively charged aqueous Ag nanoparticle mixture which comprised AgNO (85) and AgNC (90) in a 4:1 particle ratio for 20 min (FIG. 4b). Self-assembly occurred via electrostatic attraction, with the COO$^-$ functionality of the 11-MUA layer 95 on the Ag nanoparticles binding to the NH$_3$ terminal of substrate 80.

This self-assembly approach generated a monolayer of Ag nanoparticles. The binary self-assembled substrate was removed from the aqueous Ag nanoparticle mixture, rinsed with ethanol and blown dry using N$_2$ gas twice.

The substrate was then submerged in a 1H,1H,2H,2H-perfluorodecanethiol 105 solution (PFDT, 5 mM) in ethanol/hexane (1:1, v/v) for 72 hr. This step allowed PFDT to bind to the exposed surface of the Ag nanoparticles 85 and 90, by displacing 11-MUA from the surface. This helps to give a clean spectral background for SERS detection.

The resulting substrate was then coated with a layer of 25 nm Ag (103) at 0.5 Å/s via thermal evaporation to promote adhesion of the binary Ag nanoparticles to Si. The substrate was then submerged in PFDT 105 (5 mM) in ethanol/hexanes (1:1, v/v) for at least 15 hr to achieve superhydrophobicity. To create a clean spectral background in subsequent SERS measurements, the substrates were immersed in 10 mM of PFDT in ethanol/hexane (1:1, v/v) for one week, with the solution replaced with fresh PFDT solution after every 24 hr.

Effect of Different Particle Ratio of AgNC to AgNO on the Hydrophobicity of Substrate 109

To understand the effect of particle ratio of AgNC to AgNO on the hydrophobicity of the substrates, the procedure described in "Fabrication of the optimised batch of superhydrophobic substrate" was repeated with particle ratios of AgNC:AgNO at 2:1, 1:1, 1:2 and 1:4 respectively. It was observed that a AgNC:AgNO ratio of 1:4 gave the highest contact angle of 158°±8° with the highest particle density (FIGS. 9a and b)

Effect of Incubation Time of Substrate 80 in the Ag Nanoparticle Mixture (85+90) on the Hydrophobicity of Substrate 109

To investigate the effect of incubation time of substrate 80 in the Ag nanoparticle suspension on the hydrophobicity of the substrate, the procedure described above was repeated with different incubation time of 20 to 100 min to give the respective substrates 109.

The static contact angles and particle density of the various substrates 109, treated with Ag nanoparticles for different incubation times, were determined and as shown in FIGS. 10a and b respectively. An immersion time of 20 min was chosen as the optimised time as this was the shortest incubation time which gave the substrates with consistently high static contact angle. At the particle ratio of 4:1, the particle density was determined to be 4.4±0.2 particles/μm$^2$ (estimated from counting the number of particles in the SEM images). At this particle ratio, the root mean square surface roughness is also the highest at 116.4±6.2 nm.

Effect of Having a Binary Assembly of AgNC and AgNO on the Hydrophobicity of Substrate 109, as Compared to Having AgNC or AgNO Alone To understand the effect of having a binary assembly of AgNC and AgNO on the hydrophobicity of the substrate, substrates containing only AgNC or AgNO were synthesised according to the procedure above, with an incubation time of 20 min. The static contact angles and the AFM images of the respective substrates 109 were determined and as shown in FIGS. 11a and b. It was observed that the binary assembly gave the highest static contact angle of 1580±80.

Liquid Concentrating Effect of Substrate 109 in Comparison to a Hydrophilic Substrate The liquid concentrating effect of substrate 109 was determined according to the procedure described above in "liquid concentrating effect of the substrates". Comparing the dried contact area of the droplet of silica suspension on substrate 109 to the hydrophilic substrate, the dried contact area on substrate 109 was 0.13 mm$^2$ which was significantly lower than the area of 24 mm$^2$ on the hydrophilic substrate (FIGS. 8g and h). The calculated concentrating factor was determined to be approximately 180.

As such, the significant reduction of the contact area of the analyte sample on the superhydrophobic substrate 109 can lead to a concentrating of the analytes into a smaller area which is required for sensitive detection.

Superhydrophobic Substrate Containing a Binary Assembly of AgNS and AgNO

The AgNS/AgNO superhydrophobic substrate was synthesised according the method described above for superhydrophobic substrate 109, except that AgNC was replaced with AgNS.

Electrostatic self-assembly was first performed by submerging the positively-charged Si substrate into 2 mL of negatively charged aqueous Ag nanoparticle mixture comprising AgNO and AgNS in a 2:1 particle ratio for 40 min (each portion of particle contained 1.2×10$^{11}$ particles/mL). The binary self-assembled substrate was removed from the aqueous Ag nanoparticle mixture, rinsed with ethanol and blown dry using N$_2$ gas twice. The substrate was then immersed into a solution of PFDT solution (5 mM) for 72 hr to replace the 11-MUA ligand and sodium citrate on the surface of the Ag nanoparticles.

The resulting substrate was then coated with a layer of 25 nm Ag at 0.5 Å/s via thermal evaporation to promote adhesion of the binary Ag nanoparticles to Si. The substrate was then submerged in PFDT (5 mM) in ethanol/hexanes (1:1, v/v) for at least 15 hr to achieve superhydrophobicity.

The as-synthesised substrate was characterised by SEM, with the static contact angle and particle density determined (FIGS. 19c and d). The static contact angle was determined using a droplet of deionised water (4 μL) and a value of 150.2°±1.0° was obtained.

Example 2. SERS Detection of Pregnane, p-Arsanilic Acid and Roxarsone Using the Initial Superhydrophobic Substrates 107

To validate the performance of substrates 107, direct SERS detection of urine metabolites and toxins using these substrates was carried out.

5β-pregnane-3α,20α-diol glucuronide (pregnane), which is regarded as an important urine metabolite in determining spontaneous miscarriage, was chosen as the urine metabolite for this experiment. An aqueous solution of pregnane (1×10$^{-6}$ M) was first prepared, followed by a series of 10-fold serial dilution with deionised water to give the diluted solutions of various concentrations (from 1×10$^{-7}$ M to 1×10$^{-9}$ M). 1 μL droplet of the pregnane solution was then drop-cast onto substrate 107 for analysis by SERS. The SERS spectra were obtained after drying the droplet, under laser irradiation (wavelength, 532 nm; power, 0.06 mW) and an acquisition time of 10 s.

The SERS spectra of various concentration of pregnane on substrate 107 are as shown in FIG. 13a. The intensity of the peak at 614 cm$^{-1}$ was used to obtain a calibration curve as shown in FIG. 13b. It was observed that SERS signals due to pregnane can be detected at a concentration as low as 1 nM. This represents a way to directly detect and quantify pregnane on the superhydrophobic substrate 107 using the intensity of the SERS spectra of pregnane itself.

Similarly, the SERS detection was extended to detecting ultratrace toxins like p-arsanilic acid and roxarsone. Aqueous solutions (1×10$^{-3}$ M) of p-arsanilic acid and roxarsone were first prepared by dissolving the solids in 10 mL of deionised water. This was then followed by a series of 10-fold serial dilution with deionised water to give the diluted solutions of various concentrations (from 1×10$^{-4}$M to 1×10$^{-9}$ M). 1 μL droplet of the solutions was drop-cast onto substrate 107 for analysis by SERS. The SERS spectra were obtained after drying the droplet and as shown in FIGS. 13c and d respectively, under the same parameters as described above. The SERS spectra of p-arsanilic acid and roxarsone were analysed and assigned accordingly as shown in Table 5.

For p-arsanilic acid, the intensity of the peaks at 1131 cm$^{-1}$ and 783 cm$^{-1}$ decreased with decreasing concentrations, and this was similar for roxarsone, where the peak intensity at 1355 cm$^{-1}$ showed similar trend with decreasing concentrations (Table 6).

TABLE 5

Assignment of the SERS signals of p-arsanilic acid and roxarsone

| p-Arsanilic acid | | Roxarsone | |
| --- | --- | --- | --- |
| Assignment | Wavenumber (cm$^{-1}$) | Assignment | Wavenumber (cm$^{-1}$) |
| As–C stretching | 596 | As–C stretching | 619 |
| As–Ox modes | 783 | As–OH symmetric and asymmetric stretching | 750 |
| NH$_2$ asymmetric bend | 1131 | As–Ox | 809 |
| As–OH | 1272 | Symmetric vibrational modes of nitro group | 1335 |
| Aromatic ring vibration | 1575 | | |

TABLE 6

Intensity of the respective peaks of p-arsanilic acid and roxarsone at various concentrations

| p-Arsanilic acid | | | Roxarsone | |
| --- | --- | --- | --- | --- |
| Concentration | Counts at 1131 cm$^{-1}$ | Counts at 783 cm$^{-1}$ | Concentration | Counts at 1355 cm$^{-1}$ |
| 1 × 10$^{-3}$ M | 39 | 53 | 1 × 10$^{-3}$ M | 48 |
| 1 × 10$^{-4}$ M | 24 | 15 | 1 × 10$^{-4}$ M | 36 |
| 1 × 10$^{-5}$ M | 23 | 29 | 1 × 10$^{-5}$ M | 27 |
| 1 × 10$^{-6}$ M | 20 | 21 | 1 × 10$^{-6}$ M | 9 |
| 1 × 10$^{-7}$ M | 15 | 19 | 1 × 10$^{-7}$ M | 6 |
| 1 × 10$^{-8}$ M | 3 | 6 | 1 × 10$^{-8}$ M | 3 |
| 1 × 10$^{-9}$ M | 3 | 5 | 1 × 10$^{-9}$ M | 2 |

Example 3. Determining the SERS Analytical Enhancement Factor (AEF) of the Optimised Superhydrophobic Substrate 109 when Used with AgNC/4-MPBA, in Comparison to that of Substrate 109 Alone and to a Superhydrophobic Silica Bead Array The AEF of a SERS substrate is an important indication of its performance for SERS detection. Therefore, the AEF for the superhydrophobic substrate 109 alone, and when used with AgNC/4-MPBA, and a superhydrophobic silica bead array were determined and compared, using methylene blue as the analyte.

Experimental Procedures

For SERS spectra obtained using superhydrophobic substrate 109 with AgNC/4-MPBA, a 1 µL droplet containing methylene blue (from $1\times10^{-7}$ M to $1\times10^{-14}$ M) and AgNC/4-MPBA (~$1.2\times10^7$ particles) was drop-cast onto substrate 109 and left to dry prior to recording the SERS spectra. While the 4-MPBA cannot bind to methylene blue, SERS enhancement of the methylene blue can still occur due to the physical trapping of methylene blue molecules in the spaces between adjacent AgNC particles during the drying process, and due to the concentrating effect from the superhydrophobic substrate 109.

Similarly, for SERS spectra obtained using substrate 109 alone or a silica bead array, a 1 µL droplet of methylene blue solution (from $1\times10^{-3}$ M to $1\times10^{-11}$ M) was drop-cast onto the substrate (substrate 109 alone or silica bead array) and left to dry prior to recording the SERS spectra.

For normal Raman signal measurement, the Raman spectrum of methylene blue was acquired using a 1 µL droplet of methylene blue solution ($10^{-3}$ M) on Si substrate 10. Acquisition times of 1 s and 100 s were used to acquire the SERS and Raman spectra, respectively.

The superhydrophobic silica bead array was fabricated by first immersing a silicon substrate 80 in an aqueous suspension of silica beads (1 wt %) for 10 min. This substrate was then blown dry under a stream of nitrogen, followed by functionalising with PFDT (5 mM) overnight.

Results and Discussion

The analytical enhancement factor (AEF) to quantify the SERS enhancement of analyte molecules adsorbed on the superhydrophobic SERS substrate was determined according to the formula below.

$$AEF=[I_{SERS}/I_{Raman}]\times[C_{Raman}/C_{SERS}],$$

where:

$I_{SERS}$ is the intensity of the SERS signals recorded using the SERS substrate at the lowest concentration;

$C_{SERS}$ is the corresponding concentration of the analyte measured using the SERS substrate; $I_{Raman}$ is the intensity of the ordinary Raman signals (without the SERS substrate) at the lowest concentration; and $C_{Raman}$ is the corresponding concentration of the analyte measured used for the ordinary Raman detection (without the SERS substrate).

AEF is calculated on the basis that the detection limits of individual substrates are $10^{-6}$, $10^{-11}$, and $10^{-14}$ M for superhydrophobic silica bead array, superhydrophobic substrate 109 alone, and when used with AgNC/4-MPBA, respectively.

While any other analytes can be used for determining the AEF of the SERS substrate, the AEF for this example was calculated based on the intensities at 1628 cm$^{-1}$ band of methylene blue (attributed to C═C stretching).

The AEF of the various substrates were determined and as shown in FIG. 12a-c. It was observed that the AEF for the superhydrophobic substrate 109 alone achieved an AEF of $2.4\times10^9$ which was far more superior than the AEF of $5.0\times10^2$ of the superhydrophobic silica bead array.

In addition, the use of AgNC/4-MPBA with substrate 109 further enhanced the SERS signal intensity, achieving an AEF of $2.4\times10^{12}$ (FIG. 12c). This was approximately $10^{10}$-fold and 103-fold higher than that of the superhydrophobic silica bead array and substrate 109, respectively. Other than the SERS enhancement provided by the superhydrophobic substrate 109, the use of AgNC provides an additional plasmonic surface (and "hot spots") to further enhance the SERS signals of the analytes sandwiched between the substrate 109 and AgNC. Therefore, the AgNC/4-MPBA provides a "mirror effect" to enhance the AEF of the substrate, which gives a higher SERS sensitivity for detection.

Example 4. SERS Quantification of Pregnane and/or THC Using the Superhydrophobic Substrate 109 with AgNC/4-MPBA The combination of AgNC/4-MPBA with the superhydrophobic substrate 109 was applied to the detection and quantification of urine metabolites of interest. The target urine metabolites are 5β-pregnane-3α,20α-diol glucuronide 125 (pregnane) and tetrahydrocortisone 120 (THC), in which the concentration of these two metabolites in the urine samples of pregnant women have been identified to serve as predictive indicators for the likelihood of spontaneous miscarriage (see PCT publication number WO 2018/199849).

Urine, being a complex biological matrix made up of numerous metabolites, can potentially interfere with the SERS detection and quantification of pregnane and THC in urine samples. Given this, it is critical to isolate the target urine metabolites in the solution, prior to using the superhydrophobic SERS substrate 109 for measurements and analysis. Both THC 120 and pregnane 125 contain multiple hydroxyl functional groups (—OH) which can undergo condensation reactions with boronic acid 130 (4-MBPA), grafted on the AgNC surface 135, under alkaline conditions to form boronate esters in solution (FIG. 14a). The AgNC/4-MPBA with the captured metabolites can then be isolated and drop-cast onto the superhydrophobic substrate 109 for higher SERS sensitivity (by utilising the "mirror effect" of having both AgNC and substrate 109).

Experimental Procedures

Individual SERS experiments were first conducted for pure pregnane and THC. 10 µL of pregnane or THC solution ($10^{-4}$-$10^{-9}$ M) were mixed with the AgNC/4-MPBA (~0.2 mg/mL) in KOH aqueous solution at pH 11, sonicated, and then allowed to react for 3 hr. After 3 hr, the mixture was centrifuged at 8000 rpm for 10 min. The supernatant was removed, and the products were re-dispersed into 10 µL pH 11 solution. This process was repeated two times prior to drop-casting on the superhydrophobic substrate 109 and then allowed to dry under ambient conditions. Raman spectra were collected using a laser excitation wavelength of 532 nm, at 0.2 mW and is acquisition time.

Background scans of the substrate 109 was run before the analysis of the samples were carried out. This was to ensure that there were no interfering signals arising from 11-MUA. The analysis of the actual samples was carried out only when the baseline of the Raman spectrum was flat and featureless.

For multiplex measurements, different concentration ratios of pregnane:THC were prepared using the 0.1 mM stock solutions, with the ratios ranging from 90-100%. For example, to prepare a 90% pregnane:THC solution for measurement, 90 μL of pregnane was mixed with 10 μL of THC, and this mixture was then allowed to react with the AgNC/4-MPBA under the same conditions as described earlier. SERS measurements were also conducted following the same experimental parameters as described above.

Data Analysis

Principal Component Analysis (PCA)

To improve the robustness and reliability of the detection method, hyperspectral SERS measurement was used to generate more than 2000 SERS spectra per measurement. Although building a detection method based on a large number of dataset is statistically more reliable, it would be challenging and impractical to analyse the spectra manually. In addition, the spectral changes of 4-MPBA (130) upon binding with pregnane (125) and THC (120) are not drastic across the concentration range and are restricted to specific spectral region (FIGS. 15a and b).

As such, principal component analysis (PCA) was used to analyse the extracted SERS spectra, distinguish and categorise spectral features specific to 4-MPBA, 4-MPBA-pregnane and 4-MPBA-THC across the entire measured spectral range. PCA is a standard statistical procedure to analyse large datasets, and commercially available software (Panorama) was used to conduct the PCA.

Typically, 25 untreated spectra for AgNC/4-MPBA (at pH 11), AgNC/4-MPBA incubated with THC, and AgNC/4-MPBA incubated with pregnane, respectively, were input into the software (a total of 75 spectra). Standard normal variate correction and Savitzky-Golay derivative algorithm were applied to reduce spectral noise and to eliminate interference from the background signals. During PCA analysis, the whole spectral range measured experimentally was selected, and two PCs were applied, which enabled spectral identification with at least 98% accuracy.

Partial Least Square (PLS) Regression

In addition, partial least square regression (PLS) was used to test the predictive power of the SERS measurements for different concentrations of pregnane and THC. This was done by establishing standard calibration curves for the individual urine metabolites. For pure analytes, 25 spectra were input for each concentration measured, resulting in the use of 150 spectra to derive a calibration curve between $10^{-4}$-$10^{-9}$ M for each analytes.

Standard normal variate correction and Savitzky-Golay derivative algorithm were applied to reduce spectral noise and eliminate interference. During the analysis, the entire spectral range measured experimentally was selected, and a suitable number of loading vectors were employed to provide the minimum root-mean-square error for cross validation (RMSECV). Three loading vectors were used for the spectra involving pregnane and two were used for THC. The minimum number of loading vectors was selected based on two considerations: (1) to minimise the possibility of overfitting (i.e. incorporation of chance correlations and noise components); and (2) to achieve <5% deviation from the minimal RMSECV.

Results and Discussion

Distinct spectral changes were observed for the SERS spectra of 4-MPBA after incubating with THC and pregnane respectively (FIG. 14b). Notably, AgNC/4-MPBA showed characteristic 4-MPBA vibration modes at 1182 cm$^{-1}$ and 1328 cm$^{-1}$, which correspond to aromatic C—H bending and stretching modes of boronic acid (δBO+vCB) respectively. Upon interacting with THC and pregnane, the SERS spectra showed a dramatic change mainly in two spectral regions (i.e. regions (i) and (ii)).

For region (i), the aromatic C—H bending peak of 4-MPBA 130 broadened for both THC 120 and pregnane 125 (FIG. 14c), while in region (i), the intensity of δBO+vCB decreased drastically and blue-shifted from 1328 cm$^{-1}$ to ~1332 cm$^{-1}$, and to ~1333 cm$^{-1}$ for THC 120 and pregnane 125, respectively (FIG. 14d). The reduced SERS intensity was likely to be due to a restriction of B—O and C—B bonds by the urine metabolites 120 and 125, upon binding to the 4-MPBA 130. The experimental observations of the spectral changes were also corroborated with theoretically simulated spectra (FIGS. 14c and d). These changes clearly confirmed the successful capture of urine metabolites in their pure form by AgNC/4-MPBA and the differences in the spectral change between the binding of pregnane 125 and THC 120 to 4-MPBA 130 allow this detection method to differentiate these two metabolites selectively. Therefore, the use of the superhydrophobic substrate 109 in tandem with AgNC/4-MPBA allowed the indirect SERS detection and quantification of the target metabolites, by detecting the spectral changes of 4-MPBA upon binding to THC and/or pregnane. In this case, 4-MPBA effectively acts as both a capturing agent and a Raman reporter, to reflect the changes to the chemical bonds upon binding to the analytes.

FIG. 15c shows a representative 2D plot of the PCA-processed SERS data for individually-measured 4-MPBA, 4-MPBA-pregnane, and 4-MPBA-THC. By using two principal components (PCs) to decompose the various SERS spectra, the SERS spectra can be categorised into three distinct clusters, arising from 4-MPBA alone, 4-MPBA with pregnane and 4-MPBA with THC, respectively. These two PCs addressed 98.1% of the net variance among all three spectral datasets. For the quantification of pregnane, FIG. 15d shows the PLS regression for 4-MPBA-pregnane, with a predictive accuracy of over 99% and a detection limit of 1 nM. Similarly, FIG. 15e shows the PLS regression for 4-MPBA-THC, with a predictive accuracy of over 99% and a detection limit of 1 nM.

In addition, a PLS predictive model for simultaneous multiplex analysis of both pregnane and THC was also established. The multiplex analysis of both urine metabolites has practical importance as both metabolites are present in actual patients' samples, and the ratio of the abundance of both metabolites is an important factor in determining the risk of spontaneous miscarriage.

To create the PLS predictive models, SERS signals were collected from mixtures with various ratios of pregnane:THC. Specific ratios of pregnane and THC were allowed to react with AgNC/4-MPBA, followed by subsequent purification as discussed in the above experimental procedure. The ratios ranges from 90% to 100% pregnane, which correspond to physiologically relevant level of pregnane in actual patients' samples. FIG. 15f shows the PLS model for the multiplex measurements, established using nine loading vectors. The predictive accuracy for this multiplex model is approximately 98.5%, highlighting its ability to predict the relative abundance of both pregnane and THC from SERS measurement.

Example 5. SERS Quantification of Pregnane and/or THC in Artificial Urine Samples Using the Superhydrophobic Substrate 109 with AgNC/4-MPBA The experimental protocol and results as discussed in Example 4 relates to detection of metabolites in the absence of complex sample matrix that is present in actual urine samples. Therefore, to investigate the applicability of the current invention in more realistic sample matrix, the detection method was extended to detection in artificial urine.

Experimental Procedures

Preparation and Spiking of Artificial Urine

Artificial urine allows the simulation of real urine at controlled conditions, in which the relative abundance of various components can be adjusted accordingly. Firstly, artificial urine was prepared by mixing 24.2 g urea, 10.0 g sodium chloride, 6.0 g of monopotassium phosphate, 6.4 g sodium phosphate in 100 mL of deionised water.

Specific ratios of pregnane and THC were then added to this artificial urine sample to derive a standard calibration curve, and to simulate samples relating to stable pregnancy and miscarriage. The concentrations of the stock solution of pregnane and THC used for this example were 1 nM. To spike artificial urine with different ratios of pregnane and THC for multiplex measurements, 10 μL of pregnane and/or THC solution were added into 90 μL of artificial urine, with the ratio of pregnane ranging from 90-100%. For example, to spike artificial urine with 90% pregnane, 9 μL of pregnane and 1 μL of THC were added to 90 μL of artificial urine.

Based on previous study, stable pregnancy corresponds to a 76:1 pregnane:THC ratio (98.7% of pregnane), whereas spontaneous miscarriage corresponds to a ratio of 38:1 (97.4% of pregnane). Therefore, the concentration range of pregnane:THC used in this example covered the physiological concentration of pregnane and THC.

ZIPTIP Pre-Treatment of Artificial Urine Samples

ZIPTIP is a commercially available mini-column packed with C-18 resin, which is routinely used for desalting, concentrating, and purifying biological samples. Before sample pre-treatment, the ZIPTIP column was activated by eluting with 20 μL of methanol and 20 μL of deionised water.

10 μL of spiked artificial urine sample was then eluted through the ZIPTIP column 210 and then washed with 10 μL of water (220) to remove salts 225 (FIG. 16*a*). 10 μL of methanol (230) was then used to elute the analytes 235 from the column. The methanol solvent was then vaporised, and the filtered sample was dissolved in 10 μL of KOH aqueous solution at pH 11 (236) to form the sample 238.

Treatment of Sample with AgNC/4-MPBA for SERS Detection

The sample analyte 238 was then mixed with AgNC/4-MPBA (0.2 mg/mL, 10 μL), sonicated, and allowed to react for 3 hr (FIG. 16*b*). After 3 hr, the mixture was centrifuged at 8000 rpm for 10 min. The supernatant was removed, and the products were re-dispersed in 10 μL of KOH aqueous solution at pH 11. This process was repeated two times prior to drop-casting on the superhydrophobic substrate 109 for SERS detection. A minimum of three individual samples was prepared by drop-casting the samples onto different locations of substrate 109 to obtain an average reading. The SERS spectra were collected and used for chemometric analysis 240.

Data Analysis

The SERS spectra were subject to Principal Component Analysis (PCA) and Partial Least Square (PLS) analysis, with 25 spectra from each simulated condition analysed using the same protocol as described in Example 4.

PLS analysis was used to establish standard calibration curves for the multiplexed detection of analytes in artificial urine, with the PLS model built up from 90-100% of pregnane in spiked artificial urine.

Results and Discussion

FIG. 17*a* shows the PLS predictive model derived from artificial urine samples spiked with various concentrations of pregnane. A good linear correlation was observed for the tested range of pregnane concentration, with a high accuracy of >97%, indicating that the experimental protocol and data analysis approach can be applied to artificial urine samples without loss of accuracy.

The PCA analysis of the simulated stable pregnancy and the simulated spontaneous miscarriage samples (using two PCs to decompose the various SERS spectra) were also carried out. The SERS spectra were categorised into two distinct clusters, corresponding to stable pregnancy and spontaneous miscarriage respectively (FIG. 17*b*), with prediction results of 98.9±0.3% and 97.2±0.8% respectively. The two PCs addressed 89.8% of the net variance among the two spectral datasets. The SERS spectra of various ratio of pregnane:THC (from 90-100%) are as shown in FIG. 17*c*. The SERS spectra which corresponds to stable pregnancy (98.7% of pregnane) and miscarriage (97.4% of pregnane) are as shown in FIG. 17*d*.

The PLS regression also accurately predicted the relative amounts of pregnane in both simulated urine samples (FIG. 17*e*). For simulated stable pregnancy sample with a pregnane:THC ratio of 76:1, the theoretical pregnane percentage is 98.9% and the PLS prediction accuracy of the current model corresponded to 98.9±0.3% with a very narrow error window. For simulated spontaneous miscarriage sample with a pregnane:THC ratio of 38:1, the theoretical pregnane percentage is 97.3% and the PLS prediction accuracy corresponded to 97.2±0.8% with a very narrow error window. Therefore, it is clear that the experimental and analytical approaches can be successfully applied to artificial urine samples without any loss of accuracy.

Example 6. SERS Quantification of Pregnane and/or THC in Real Urine Samples Using the Superhydrophobic Substrate 109 with AgNC/4-MPBA To further demonstrate the applicability of the current experimental protocol and analytical approach in the diagnosis of spontaneous miscarriage, real urine samples were used in this example.

A standard calibration curve was first established using urine samples collected from non-pregnant women, with serum progesterone levels of 1.01 nmol/L. These urine samples were spiked with specific ratios of pregnane and THC, and were followed by standard ZIPTIP treatment, reaction with AgNC/4-MPBA, purification by centrifugation, SERS measurements and analyses (as described in Examples 4 and 5). The concentrations of the stock solution of pregnane and THC were 0.1 nM. New calibration curves were prepared for every analyte used because the calibration curves are highly dependent on the SERS-response of that specific analyte. It is also preferred to prepare new calibration curves for every substrate for better accuracy of the quantification.

For urine samples that represent stable pregnancy and spontaneous miscarriage, six urine samples were chosen based on the serum progesterone level of the patients, with their pregnane:THC abundance ratio of the urine samples determined by LC/MS (Table 7). The serum progesterone levels for patients with stable pregnancy were 74.88, 106.45, and 64.42 nmol/L, with the corresponding pregnane:THC abundance ratio in their urine samples determined to be 98.7, 99.3, and 99.1% respectively. The serum progesterone levels for patients with spontaneous miscarriage sample were 7.72, 8.9, and 15.42 nmol/L, with the corresponding pregnane:THC abundance ratio in their urine samples determined to be 94.1, 93.1 and 93.6% respectively. These urine samples were subject to the standard ZIPTIP treatment, reaction with AgNC/4-MPBA, purification by centrifugation, measurements and analyses (as described in Examples 5).

FIG. 18a shows the PLS predictive model derived from real non-pregnant urine samples spiked with various concentrations of pregnane. A good linear correlation was observed for the tested pregnane concentration range with a high accuracy of >99%, indicating that the current experimental protocol and data analysis approach can be applied to real urine samples without loss of accuracy. The SERS spectra of non-pregnant women urine spiked with different pregnane concentrations, and the SERS spectra of actual urine sample from pregnant women are as shown in FIGS. 18b and c respectively. A PCA clustering was also applied to the two actual urine samples, one with spontaneous miscarriage (M1) and another with successful delivery (S1), using 25 untreated spectra each (FIG. 18d).

In addition, PLS regression also accurately predicted the relative amounts of pregnane in the real urine samples. For urine samples corresponding to stable pregnancy with a pregnane:THC ratio of 98.7, 99.3, and 99.3%, PLS prediction using the current model gave the respective concentrations of 101.3±0.2, 99.2±0.2, 98.6±0.7%, with a very narrow error window (Table 7). For samples corresponding to spontaneous miscarriage with a pregnane:THC ratio of 94.1, 93.1, and 93.6%, the current model gave the respective concentrations of 96.9±0.8, 94.8±0.5 and 94.7±0.6%, also with a very narrow error window (Table 7).

As the SERS measurements correlated very well with known readings derived from the LC/MS measurements, it is clear the current invention can achieve point-of-care non-invasive detection of urine metabolites from urine, which can serve as a non-invasive diagnosis of spontaneous miscarriage. In addition, this capability was most evidently demonstrated in real urine samples with different levels of urobilin (as qualitatively observed in the differences in urine colours). There was minimal impact to the accuracy of PLS prediction for miscarriage risk even in the presence of different amounts of urobilin.

TABLE 7

Comparing the percentage of pregnane as determined from the PLS prediction model to that determined by LC/MS, for patients with successful delivery (S1-S3) and for patients who suffered spontaneous miscarriage (M1-M3)

| Patient No. | Progesterone concentration (nmol/L) | Actual urine pregnane % by LC/MS (pregnane/ (THC + pregane)) | Pregnane % by PLS model (pregnane/(THC + pregnane)) | Pregnancy outcome |
| --- | --- | --- | --- | --- |
| S1 | 74.88 | 98.7% | 101.3 ± 0.2 | Childbirth |
| S2 | 106.45 | 99.3% | 99.2 ± 0.2 | Childbirth |
| S3 | 64.42 | 99.1% | 98.6 ± 0.7 | Childbirth |
| M1 | 7.72 | 94.1% | 96.9 ± 0.8 | Miscarriage |
| M2 | 8.9 | 93.1% | 94.8 ± 0.5 | Miscarriage |
| M3 | 15.42 | 93.6% | 94.7 ± 0.6 | Miscarriage |

The invention claimed is:

1. A composite superhydrophobic material suitable for use in surface-enhanced Raman scattering, the material comprising:
a substrate layer comprising a set of positively or negatively charged functional groups;
a single-layered metal nanoparticle coating on top of the substrate layer and comprising a set of negatively or positively charged functional groups;
a metal layer on top of the single-layered metal nanoparticle coating; and
a first superhydrophobic layer on top of the metal layer, wherein:
the metal nanoparticle coating comprises a mixture of a first set and a second set of metal nanoparticles arranged as a single layer on the substrate, where the first set of metal nanoparticles has a diameter that is from 0.1 to 90% smaller than the diameter of the second set;
the metal of the first set of metal nanoparticles is at least one of gold and silver;
the metal of the second set of metal nanoparticles is at least one of gold and silver; and
the charged functional groups on the substrate layer and metal nanoparticle coating are electronically complementary to one another, and wherein the first set and the second set of the metal nanoparticles are electrostatically bound to the substrate layer.

2. The composite superhydrophobic material according to claim 1, wherein one or both of the following apply:
the density of the metal nanoparticle coating on the surface of the substrate layer is from 2 to 20 particles/μm2, and
the composite material further comprises a second superhydrophobic layer sandwiched between the metal nanoparticle coating and the metal layer.

3. The composite superhydrophobic material according to claim 1, wherein the material displays a static contact angle with water of greater than 150°.

4. The composite superhydrophobic material according to claim 1, wherein one or both of the following apply:
the first set of nanoparticles have an average diameter of from 10 to 250 nm, and
the second set of nanoparticles have an average diameter of from 250 to 1,000 nm.

5. The composite superhydrophobic material according to claim 1, wherein one or more of the following apply:
(ia) the first set of metal nanoparticles has a diameter that is from 0.2 to 60% smaller than the diameter of the second set;
(iia) the composite has a root mean square surface roughness of from 30 to 150 nm; and
(iiia) the total number of particles in the second set of nanoparticles to the total number of particles in the first set of nanoparticles on the composite material is from 1:10 to 10:1.

6. The composite superhydrophobic material according to claim 1, wherein the set of charged functional groups on the substrate layer are positively charged and the charged functional groups on the metal nanoparticle coating are negatively charged.

7. The composite superhydrophobic material according to claim 6, wherein:
the set of positively charged functional groups on the substrate layer are ammonium ions; and
the set of negatively charged functional groups on the first and second set of metal nanoparticles are carboxylate ions or alkoxide ions.

8. The composite superhydrophobic material according to claim 1, wherein the set of charged functional groups on the substrate layer are negatively charged and the charged functional groups on the metal nanoparticle coating are positively charged.

9. The composite superhydrophobic material according to claim 8, wherein one or both of the following apply:
the set of negatively charged functional groups on the substrate layer are carboxylate ions or alkoxide ions; and
the set of positively charged functional groups on the first and second set of metal nanoparticles are ammonium ions.

10. The composite superhydrophobic material according to claim 1, wherein at least one of the group consisting of the following applies:
(ib) the metal layer is from 5 to 53 nm thick;
(iib) the metal layer comprises a silver layer, a gold layer or a silver and gold layer;
(iiib) there is direct attachment between the metal layer and the substrate layer through gaps between nanoparticles in the metal nanoparticle coating;
(ivb) the first superhydrophobic layer comprises a C10 to C20 thiol that is unsubstituted or substituted by one or more fluoro groups; and
(vb)) the composite superhydrophobic material further comprises a second superhydrophobic layer comprises comprising a C10 to C20 thiol that is unsubstituted or substituted by one or more fluoro groups.

11. The composite superhydrophobic material according to claim 1, wherein the first set of metal nanoparticles are nanocubes and the second set of metal nanoparticles are nanopolyhedrons having more than six faces and are selected from one or more nanopolyhedra having from 7 to 30 faces.

12. The composite superhydrophobic material according to claim 11, wherein the second set of metal nanoparticles are nanooctahedra.

13. The composite superhydrophobic material according to claim 1, wherein the first and second set of nanoparticles are silver nanoparticles.

14. A kit of parts comprising:
(ai) composite superhydrophobic material as described in claim 1; and
(bi) a urine analysis formulation comprising silver and/or gold nanoparticles coated with a boronic acid comprising a thiol group.

15. A method of predicting increased risk of spontaneous miscarriage, the method comprising the steps of:
(a) providing an aqueous solution comprising the non-salt components of a urine sample obtained from a subject;
(b) reacting the aqueous solution with a urine analysis formulation comprising silver and/or gold nanoparticles coated with a boronic acid comprising a thiol group for a first period of time to provide a complexed sample;
(c) placing the complexed sample onto a composite superhydrophobic material as described in claim 1 and removing the water by evaporation to provide a dried sample; and
(d) subjecting the dried sample to Raman spectroscopy to determine the abundance of pregnane and tetrahydrocortisone and then predicting the risk of spontaneous miscarriage based on the formula:
(Pregnane Abundance)/((Pregnane Abundance+Tetrahydrocortisone Abundance)) x100%
wherein a value lower than a threshold value is indicative of increased risk of spontaneous miscarriage.

16. The method according to claim 15, wherein the aqueous solution provided in step (a) of the process is obtained by the following steps:
(i) adding a urine sample comprising salt and non-salt components obtained from a subject onto a reverse phase column to provide a loaded column;
(ii) removing the salt components from the loaded column by eluting with water, then removing and isolating the non-salt components from the loaded column by eluting with a C1-4 alcohol (e.g. methanol) and then removing the C1-4 alcohol; and
(iii) adding an aqueous solution to the isolated non-salt components to provide the aqueous solution of step (a).

17. The method according to claim 15, wherein the Raman spectroscopy is conducted using a laser excitation wavelength of 532 nm, using a laser power of from 0.01 to 1 mW and an acquisition time of from 1 to 60 seconds.

18. A method of making a composite superhydrophobic material suitable for use in surface-enhanced Raman scattering, the method comprising:
(ia) providing a metal-coated composite material comprising: a substrate layer comprising a set of positively or negatively charged functional groups; a metal nanoparticle coating on top of the substrate layer, comprising a set of negatively or positively charged functional groups, where the metal nanoparticle coating comprises a first set and a second set of metal nanoparticles arranged as a single layer on the substrate, where the first set of metal nanoparticles has a diameter that is from 0.1 to 90% smaller than the diameter of the second set; and a metal layer on top of the metal nanoparticle coating; and
(ib) immersing the metal-coated composite material in a solution comprising a superhydrophobic material to form a superhydrophobic layer on top of the metal layer, thereby forming the composite superhydrophobic material, wherein: the metal of the first set of metal nanoparticles is gold and/or silver is selected from the group consisting of gold, silver, and a combination of gold and silver; the metal of the second set of metal nanoparticles is gold and/or silver is selected from the group consisting of gold, silver, and a combination of gold and silver; and the charged functional groups on the substrate layer and metal nanoparticle coating are electronically complementary to one another.

19. The method according to claim 18, wherein the set of charged functional groups on the substrate layer are positively charged and the charged functional groups on the metal nanoparticle coating are negatively charged.

20. The method according to claim 18, wherein the set of charged functional groups on the substrate layer are negatively charged and the charged functional groups on the metal nanoparticle coating are positively charged.

21. The composite superhydrophobic material according to claim 2, wherein the second superhydrophobic layer comprises a C10 to C20 thiol that is unsubstituted or substituted by one or more fluoro groups.

22. The composite superhydrophobic material according to claim 1, wherein:
   the first set of nanoparticles have an average diameter of from 10 to 250 nm;
   the second set of nanoparticles have an average diameter of from 250 to 1,000 nm; and
   the total number of particles in the second set of nanoparticles to the total number of particles in the first set of nanoparticles on the composite material is from 2:1 to 4:1.

* * * * *